United States Patent
Watanabe

(10) Patent No.: US 11,347,972 B2
(45) Date of Patent: May 31, 2022

(54) TRAINING DATA GENERATION METHOD AND INFORMATION PROCESSING APPARATUS

(71) Applicant: FUJITSU LIMITED, Kawasaki (JP)

(72) Inventor: Shunichi Watanabe, Kawasaki (JP)

(73) Assignee: FUJITSU LIMITED, Kawasaki (JP)

( * ) Notice: Subject to any disclaimer, the term of this patent is extended or adjusted under 35 U.S.C. 154(b) by 11 days.

(21) Appl. No.: 17/086,485

(22) Filed: Nov. 2, 2020

(65) Prior Publication Data

US 2021/0201079 A1    Jul. 1, 2021

(30) Foreign Application Priority Data

Dec. 27, 2019  (JP) .............................. JP2019-237904

(51) Int. Cl.
*G06K 9/62* (2022.01)
*G06F 17/15* (2006.01)
*G06N 3/08* (2006.01)
*G06V 10/44* (2022.01)

(52) U.S. Cl.
CPC ........... *G06K 9/6257* (2013.01); *G06F 17/15* (2013.01); *G06N 3/08* (2013.01); *G06V 10/44* (2022.01)

(58) Field of Classification Search
CPC combination set(s) only.
See application file for complete search history.

(56) References Cited

U.S. PATENT DOCUMENTS

| | | | | |
|---|---|---|---|---|
| 2013/0204664 A1* | 8/2013 | Romagnolo | ....... | G06Q 30/0203 705/7.32 |
| 2014/0114890 A1* | 4/2014 | Fujimaki | ................ | G06N 7/005 706/12 |
| 2017/0061329 A1* | 3/2017 | Kobayashi | ............. | G06N 20/00 |
| 2017/0371073 A1* | 12/2017 | Suzuki | ..................... | G01W 1/10 |
| 2018/0046926 A1* | 2/2018 | Achin | ..................... | G06N 20/20 |
| 2018/0060744 A1* | 3/2018 | Achin | ....................... | G06N 5/04 |
| 2018/0090152 A1* | 3/2018 | Ichimura | ............. | G10L 21/0216 |
| 2018/0218380 A1* | 8/2018 | Fujimaki | ............ | G06Q 30/0201 |
| 2019/0042940 A1* | 2/2019 | Sakairi | ...................... | G06N 3/08 |
| 2019/0318260 A1 | 10/2019 | Yasutomi et al. | | |

(Continued)

FOREIGN PATENT DOCUMENTS

| | | |
|---|---|---|
| JP | 6481794 B1 | 3/2019 |
| JP | 2019-185483 A | 10/2019 |

*Primary Examiner* — Omar S Ismail
(74) *Attorney, Agent, or Firm* — Xsensus LLP

(57) ABSTRACT

A non-transitory computer-readable recording medium has stored therein a program that causes a computer to execute a process comprising: acquiring a first feature from a machine learning model that estimates a first result of a target after a first period in response to an input of a first chronological state of the target in the first period, the first feature being a feature of the first chronological state; acquiring a second feature by inputting a second chronological state to the machine learning model, the second feature being a feature of the second chronological state in a second period including a period after the first result is determined; and generating, based on the first feature and the second feature, training data that takes the second chronological state as an explanatory variable and takes a second result as an objective variable, the second result being obtained by changing the determined first result.

16 Claims, 20 Drawing Sheets

(56) References Cited

U.S. PATENT DOCUMENTS

2020/0118263 A1\* 4/2020 Nogami .................... G06T 7/73
2020/0175962 A1\* 6/2020 Thomson .............. G06F 40/279
2020/0175987 A1\* 6/2020 Thomson ................ G10L 15/22
2020/0211580 A1\* 7/2020 Lee .................... G10L 21/0216

\* cited by examiner

FIG. 10

| EMPLOYEE NO. | DATE | DAY OF THE WEEK | ATTENDANCE CATEGORY | ATTENDANCE TIME | LEAVING TIME | OVERTIME HOURS | BUSINESS TRIP |
|---|---|---|---|---|---|---|---|
| 100 | 20150401 | WEDNESDAY | DAY OFF | | | | |
| 100 | 20150402 | THURSDAY | ATTENDANCE | 08:49 | 0:00 | 360 | NONE |
| 100 | 20150403 | FRIDAY | ATTENDANCE | 08:49 | 0:00 | 360 | NONE |
| 100 | 20150404 | SATURDAY | ATTENDANCE | 09:00 | 17:00 | 420 | NONE |
| ... | | | | | | | |
| 100 | 20150823 | TUESDAY | ATTENDANCE | 08:49 | 17:50 | 0 | NONE |
| 100 | 20150824 | WEDNESDAY | RECUPERATION | | | | |
| ... | | | | | | | |
| 100 | 20161001 | TUESDAY | RECUPERATION | | | | |
| 100 | 20161002 | WEDNESDAY | ATTENDANCE | 08:30 | 17:50 | 0 | NONE |
| 100 | 20161003 | THURSDAY | ATTENDANCE | 08:30 | 17:50 | 0 | NONE |
| ... | ... | | | | | | |

FIG. 11

| EMPLOYEE | DATA ID | EXPLANATORY VARIABLE | OBJECTIVE VARIABLE |
|---|---|---|---|
| TARO YAMADA | 001 | ATTENDANCE RECORD DATA FROM JANUARY TO JUNE | WITH RECUPERATION |
| | 002 | ATTENDANCE RECORD DATA FROM FEBRUARY TO JULY | WITHOUT RECUPERATION |
| | ... | ... | ... |
| JANE SUZUKI | 011 | ATTENDANCE RECORD DATA FROM JANUARY TO JUNE | WITHOUT RECUPERATION |
| | 012 | ATTENDANCE RECORD DATA FROM FEBRUARY TO JULY | WITHOUT RECUPERATION |
| | ... | ... | ... |
| ... | ... | ... | ... |

FIG. 13

| DATA ID | CORE TENSOR AT LEARNING | CORE TENSOR AT PREDICTION | CORE TENSOR AT UPDATE |
|---|---|---|---|
| X | CORE TENSOR | — | — |
| ... | ... | ... | ... |

TRAINING DATA GENERATION METHOD AND INFORMATION PROCESSING APPARATUS

CROSS-REFERENCE TO RELATED APPLICATION

This application is based on and claims the benefit of priority of the prior Japanese Patent Application No. 2019-237904, filed on Dec. 27, 2019, the entire contents of which are incorporated herein by reference.

FIELD

The embodiments discussed herein are related to a training data generation method and an information processing apparatus.

BACKGROUND

In recent years, machine learning has been used in various fields such as manufacturing industry and medical cares. In the machine learning, for example, training data are used to learn a predetermined task. The predetermined task includes determining defects in a manufactured article from an image, determining the health condition of an employee from attendance record data of the employee, and the like. As an example of the machine learning, the deep learning that utilizes a neural network (NN) as a learning model is known.

However, it may be difficult to collect data itself for one of the label of the positive example or negative example as the training data used for the machine learning. For example, in the medical field, it is difficult to collect training data indicating an abnormal state because there are few data indicating the abnormal state. Therefore, new training data are generated by giving an actual result as a teacher label to the input data used for prediction.

Related techniques are disclosed in, for example, Japanese Laid-Open Patent Publication No. 2019-185483.

SUMMARY

According to an aspect of the embodiments, a non-transitory computer-readable recording medium has stored therein a program that causes a computer to execute a process, the process comprising: acquiring a first feature from a machine learning model that estimates a first result of a target after a first period in response to an input of a first chronological state of the target in the first period, the first feature being a feature of the first chronological state; acquiring a second feature by inputting a second chronological state to the machine learning model, the second feature being a feature of the second chronological state in a second period including a period after the first result is determined; and generating, based on the first feature and the second feature, training data that takes the second chronological state as an explanatory variable and takes a second result as an objective variable, the second result being obtained by changing the determined first result.

The object and advantages of the invention will be realized and attained by means of the elements and combinations particularly pointed out in the claims. It is to be understood that both the foregoing general description and the following detailed description are exemplary and explanatory and are not restrictive of the invention, as claimed.

BRIEF DESCRIPTION OF DRAWINGS

FIG. 10 is a diagram illustrating an example of information stored in a sensor data DB;

FIG. 11 is a diagram illustrating an example of information stored in a training data DB;

FIG. 13 is a diagram illustrating an example of information stored in a core tensor data DB;

DESCRIPTION OF EMBODIMENTS

As another method of collecting the training data indicating the abnormal state, it is conceivable to give a teacher label to newly acquired input data to generate new training data based on a similarity between the input data used for prediction and the newly acquired input data. However, according to this method, since the input data are compared with each other, there is a high possibility that the teacher label is estimated such that a part important for the task, which is used for the original prediction, has been missed. That is, when a learning model is updated using the new training data, the accuracy may be deteriorated.

Hereinafter, embodiments disclosed in the present disclosure will be described in detail with reference to the accompanying drawings. The present disclosure is not limited to the embodiments. Further, the embodiments may be used in proper combination unless contradictory.

First Embodiment

Figure 1A:
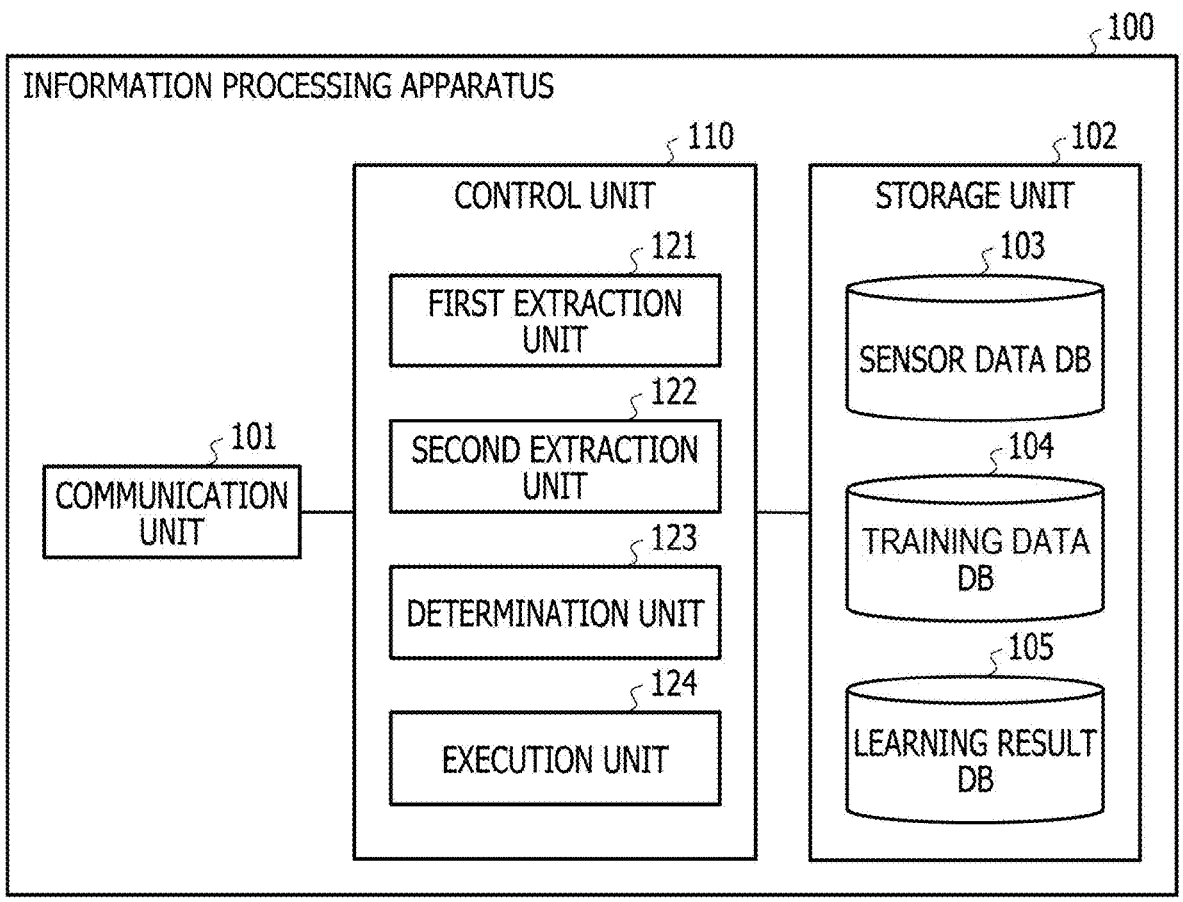
FIG. 1A is a diagram illustrating a functional configuration of an information processing apparatus according to a first embodiment.

FIG. 1A is a diagram illustrating a functional configuration of an information processing apparatus 100 according to a first embodiment. As illustrated in FIG. 1A, the information processing apparatus 100 includes a communication unit 101, a storage unit 102, and a control unit 110.

The communication unit 101 is a processing unit that controls communication with other devices, and is, for example, a communication interface. For example, the communication unit 101 receives a processing start instruction, training data, a feature amount of training data, and the like from a terminal device 200 of an administrator illustrated in FIG. 1B. The communication unit 101 also outputs the learning result, the prediction result, and the like to the terminal device 200. Further, the communication unit 101 delivers a learning model to a communication unit 201 illustrated in FIG. 1B.

The storage unit 102 is implemented by a storage device (e.g., a memory or a hard disk) that stores programs and data. The storage unit 102 stores a sensor data database (DB) 103, a training data DB 104, and a learning result DB 105. The sensor data DB 103 is a database that stores a plurality of states of a target. For example, the plurality of states of a target corresponds to the attendance category of attendance record data of an employee. In addition, as another example, the plurality of target states may be sensor values detected by a sensor installed for each process of a manufacturing line.

The training data DB 104 is a database that stores information about training data. Specifically, data stored in the training data DB 104 is used for training a learning model (the learning model learns training data in the training). A learning model is a program that incorporates parameters, and outputs a fixed result in response to an input. The training data DB 104 stores, for example, each piece of training data that is a set of a plurality of target states and one teacher label. Further, the training data DB 104 stores training data having a state before performing a predetermined action and training data having a state after performing the predetermined action in a distinguishable state.

The learning result DB 105 is a database that stores information about learning results. For example, the learning result DB 105 stores determination results of the training data by the control unit 110, various parameters of NN optimized by machine learning, and the like. Further, the learning result DB 105 stores a trained learning model in which various parameters optimized by learning are set.

The control unit 110 is a processing unit that controls the entire processing of the information processing apparatus 100, and is implemented by, for example, a processor. The control unit 110 has a first extraction unit 121, a second extraction unit 122, a determination unit 123, and an execution unit 124.

In response to an input of a first chronological state of a target in a first period, the first extraction unit 121 acquires a first feature, which is a feature of the first chronological state, from a machine learning model that estimates a first result of the target after the first period.

That is, the first extraction unit 121 identifies first training data having a state before performing a predetermined action, from the training data stored in the training data DB 104. Then, the first extraction unit 121 extracts, from the first training data, the first feature indicating a correlation of a plurality of states and a feature of an objective variable of the first training data. Here, the predetermined action is performed, for example, on a target corresponding to training data whose teacher label is a positive example such that the teacher label becomes a negative example. In the present embodiment, the positive example is, for example, an employee with recuperation, and the negative example is an employee without recuperation. Further, the predetermined action corresponds to, for example, an action of providing counseling for an employee with recuperation. Further, the predetermined action may be an improvement on certain steps of a manufacturing line on which defective articles are manufactured.

When a second chronological state in a second period including a period after the first result is determined is input to the machine learning model, the second extraction unit 122 acquires a second feature which is a feature of the second chronological state.

That is, the second extraction unit 122 identifies second training data having a state after performing the predetermined action from the training data stored in the training data DB 104. Then, the second extraction unit 122 extracts, from the second training data, the second feature indicating the correlation of the plurality of states and a feature of an objective variable of the second training data.

Based on the first feature and the second feature, the determination unit 123 generates training data that takes the second chronological state as an explanatory variable and takes a second result obtained by changing the determined first result as an objective variable. That is, the determination unit 123 describes the second chronological state after the first result is determined, and generates the training data that takes a result after the first result is determined, as an objective variable. Then, the determination unit 123 determines whether to change the objective variable of the training data, based on the first feature and the second feature.

The determination unit 123 determines whether to change the objective variable of the second training data based on each of the first feature and the second feature. Then, when determining to change the objective variable of the second training data, the determination unit 123 generates third training data obtained by changing a teacher label of the objective variable of the second training data to a label different from a first teacher label. Subsequently, the determination unit 123 registers the generated third training data in the training data DB 104.

The execution unit 124 acquires the training data from the training data DB 104. Then, the execution unit 124 inputs a plurality of states of a target of the training data to the NN as explanatory variables. Subsequently, the execution unit 124 executes training of the NN such that an error between the output result of the NN and a teacher label indicating the result for the plurality of states becomes smaller. The result for the plurality of states is, for example, whether an employee has recuperation or not. As another example, the result for the plurality of states may be the presence or absence of defects in an article manufactured through each step of a manufacturing line.

Figure 1B:
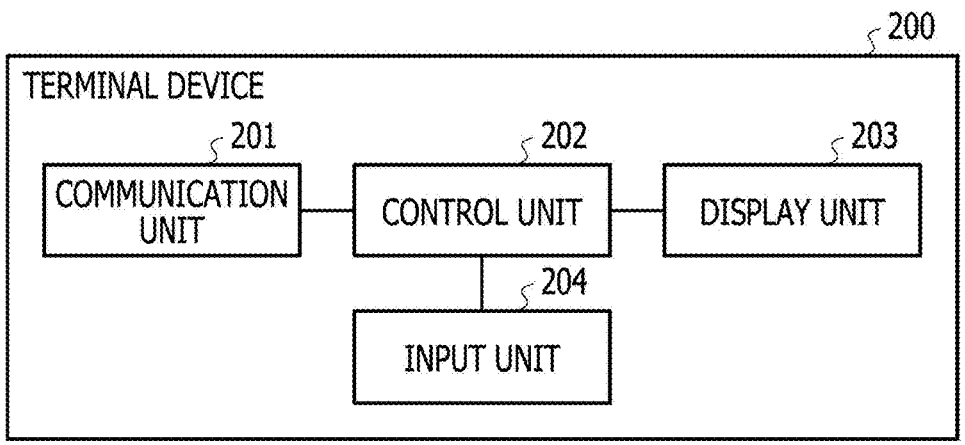
FIG. 1B is a diagram illustrating a functional configuration of a terminal device according to the first embodiment.

FIG. 1B is a diagram illustrating a functional configuration of the terminal device 200 according to the first embodiment. As illustrated in FIG. 1B, the terminal device 200 has a communication unit 201, a control unit 202, a display unit 203, and an input unit 204.

The communication unit 201 outputs a processing start instruction, training data, a feature amount of training data, and the like to the information processing apparatus 100 illustrated in FIG. 1A. The communication unit 201 also receives a learning result, a prediction result, and the like from the information processing apparatus 100. Further, the communication unit 201 receives a learning model delivered by the communication unit 101.

The control unit 202 controls the entire processing of the terminal device 200. The control unit 202 is implemented by, for example, a processor. The control unit 202 uses the learning model to identify the prediction result from the plurality of states of the target, and causes the display unit 203 to display the identified prediction result. For example, when the information regarding the attendance category of the attendance record data of an employee is input to the input unit 204, the control unit 202 predicts the presence or absence of recuperation of the employee and causes the display unit 203 to display the prediction result.

The display unit 203 displays the learning result or the prediction result. The display unit 203 is, for example, a display device or the like.

The input unit 204 inputs various kinds of information. The input unit 204 is implemented by, for example, a keyboard, a touch panel, or a mouse.

Figure 2:
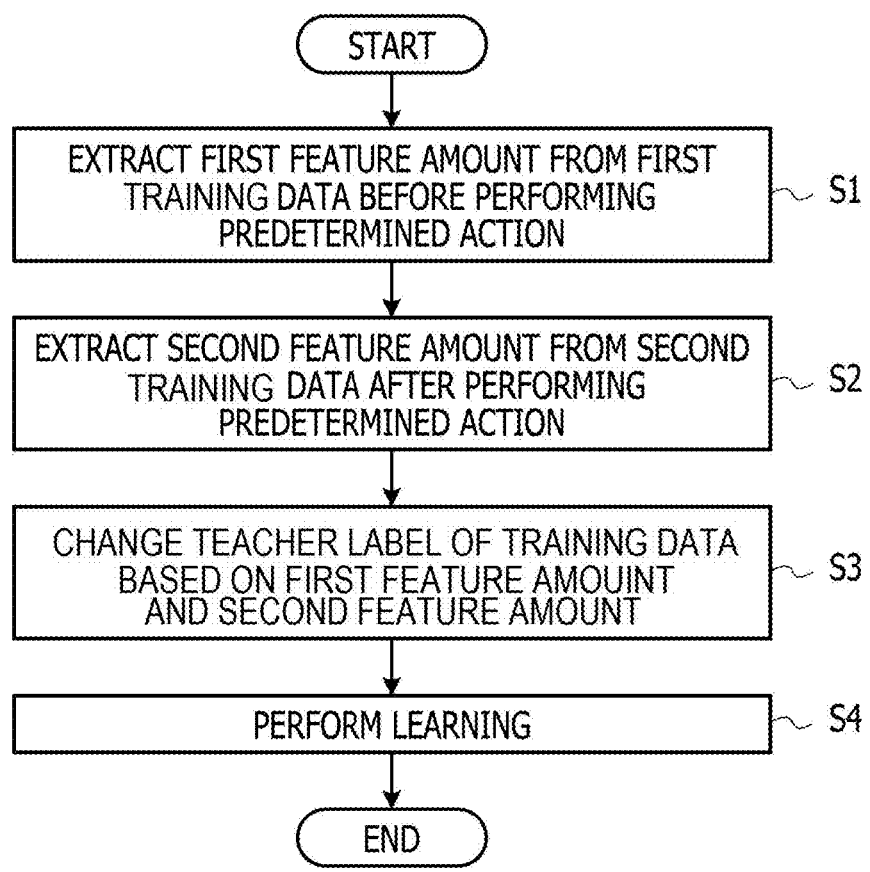
FIG. 2 is a flowchart illustrating an example of a process executed by the information processing apparatus according to the first embodiment.
Figure 5:
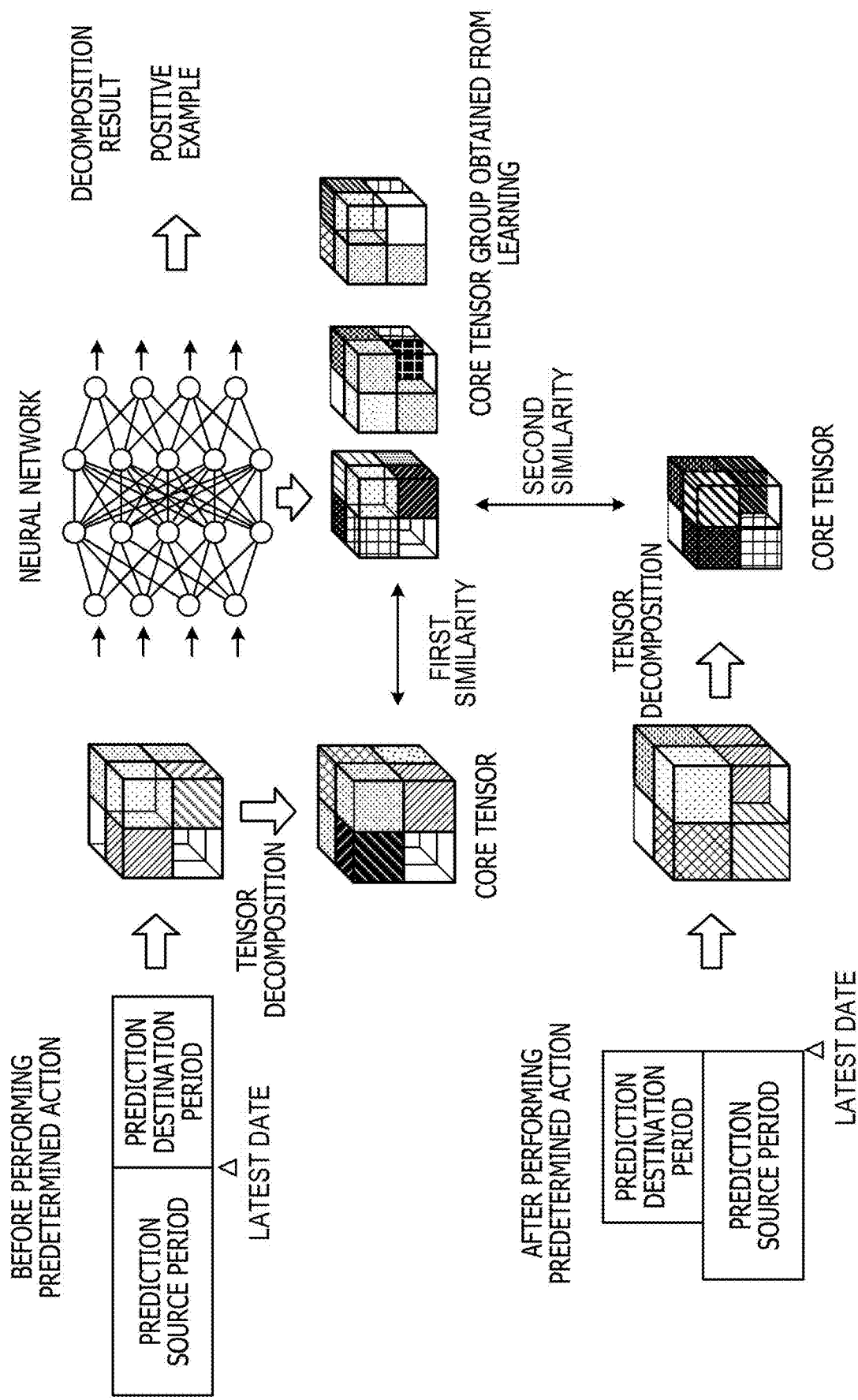
FIG. 5 is a diagram for explaining a comparison between core tensors indicating features of respective states before and after performing a predetermined action.

FIG. 2 is a flowchart illustrating an example of a process executed by the information processing apparatus 100 according to the first embodiment. First, the first extraction unit 121 identifies, from the training data stored in the training data DB 104, first training data having a state before performing a predetermined action. Then, the first extraction unit 121 extracts, from the first training data, a first feature indicating a correlation of a plurality of states and a feature of an objective variable of the first training data. For example, as illustrated in FIG. 5, the first extraction unit 121 extracts a first feature amount, which is a feature of the first chronological state of the target in the first period, using data of a prediction source period, which is the attendance record data of an employee X from the latest date to a predetermined period before. That is, the first extraction unit 121 extracts the first feature amount from the machine learning model that estimates the first result of the target after the first period in response to an input of the first chronological state in the first period (S1).

Subsequently, the second extraction unit 122 identifies second training data, which have a state after performing the predetermined action, from the training data stored in the training data DB 104. Then, the second extraction unit 122 extracts, from the second training data, a second feature indicating a correlation of a plurality of states and a feature of the objective variable of the second training data. In other words, the second extraction unit 122 extracts a second feature amount, which is a feature of the second chronological state in the second period including a period after the first result is determined, in response to an input of the second chronological state to the machine learning model (S2).

Subsequently, the determination unit 123 determines whether to change the objective variable of the second training data, based on the first feature amount and the second feature amount. When it is determined to change the objective variable of the second training data, the control unit 110 generates third training data obtained by changing a teacher label of the objective variable of the second training data to a teacher label different from the first teacher label. Specifically, when a difference between the first feature amount and the second feature amount is equal to or smaller than a preset threshold value, the determination unit 123 generates the third training data obtained by changing the objective variable of the second training data. That is, the determination unit 123 generates training data that takes the second chronological state as an explanatory variable and takes the second result, which is obtained by changing the determined first result, as an objective variable, based on the first feature amount and the second feature amount (S3).

Subsequently, the execution unit 124 learns the explanatory variable of the third training data and the objective variable of the third training data. At this time, the execution unit 124 also learns the third training data together with the first training data and the second training data. Then, the execution unit 124 generates a learning model. The execution unit 124 generates a learning model in which the parameters of the neural network are changed such that an error between the output result when the explanatory variable is input to the neural network and the correct answer information which is the objective variable is reduced (S4).

Here, descriptions will be made on an output example of the prediction result when the terminal device 200 predicts the results for a plurality of states based on the learning model.

Figure 3:
FIG. 3 is a diagram illustrating an output example when it is predicted that there is recuperation.

FIG. 3 is a diagram illustrating an output example when it is predicted that there is recuperation. As illustrated in FIG. 3, when it is predicted that there is recuperation, the terminal device 200 displays, on a screen of the display unit 203, an image indicating that it is predicted that there is recuperation. For example, the display unit 203 displays an image indicating that there is a need for counseling. As illustrated in FIG. 3, the terminal device 200 may also display a data identifier (ID) indicating attendance record data together with personal information such as an employee ID, a name, a date of birth, or the like.

Figure 4:
FIG. 4 is a diagram illustrating an output example when it is predicted that there is no recuperation.

FIG. 4 is a diagram illustrating an output example when it is predicted that there is no recuperation. As illustrated in FIG. 4, when it is predicted that there is no recuperation, the terminal device 200 displays, on the screen of the display unit 203, an image indicating that it is predicted that there is no recuperation. For example, the display unit 203 displays an image indicating that there is no need for counseling. As illustrated in FIG. 4, the terminal device 200 may also display a data ID indicating attendance record data together with personal information such as an employee ID, a name, a date of birth, or the like.

[Effects]

As described above, the information processing apparatus 100 may generate the training data that may improve the accuracy of the learning model. In addition, the information processing apparatus 100 may improve the accuracy of teacher label assignment when assigning a teacher label to the training data after performing a predetermined action.

Second Embodiment

In a second embodiment, a method of assigning a teacher label to training data using a deep tensor (DT) will be described. DT is a technique for deep learning of graph structured data. That is, the DT uses a graph structure as an input to convert the graph structure into tensor data (hereinafter, may be described as a tensor). Then, in the DT, high-precision prediction is implemented by extracting a partial structure of a graph that contributes to prediction, as a core tensor. In other words, the core tensor is a partial pattern that indicates the correlation of a plurality of states, and also represents a feature for determining the prediction result, among the training data.

FIG. 5 is a diagram for explaining a comparison between core tensors indicating features of respective states before and after performing a predetermined action. The information processing apparatus 100 may use the DT to determine whether to change a teacher label based on a change between the core tensors indicating the features of the respective states before and after performing the predetermined action.

First, when generating a learning model using a plurality of past training data, the information processing apparatus 100 acquires a core tensor group obtained from learning of the training data.

Next, using a trained learning model completed with learning, the information processing apparatus 100 acquires a core tensor that is generated when predicting a classification result for a prediction destination period from the latest date to a predetermined time after, based on the training data of the prediction source period from the latest date to the predetermined time before. The acquired core tensor indicates a feature before performing a predetermined action.

Then, after the latest date has passed the prediction destination period, the information processing apparatus 100 acquires a core tensor that is generated by performing tensor decomposition on the training data in the prediction source period from the latest date to the predetermined time before. The acquired core tensor indicates a feature after the predetermined action is performed.

Further, the information processing apparatus 100 calculates first similarity between the core tensor indicating the feature before performing the predetermined action and the core tensor at each learning, and second similarity between the core tensor indicating the feature after performing the predetermined action and the core tensor at each learning. The information processing apparatus 100 compares the first similarity and the second similarity.

[Explanation of Deep Tensor]

Here, a deep tensor used in the second embodiment will be described. A deep tensor is a technique related to deep learning that uses a tensor based on graph information as an input. The deep tensor performs training of a neural network and a method of extracting a sub graph structure that contributes to prediction (feature amount of the graph information). The training of this extraction method is implemented by optimizing the parameters of tensor decomposition for an input tensor.

Figure 6:
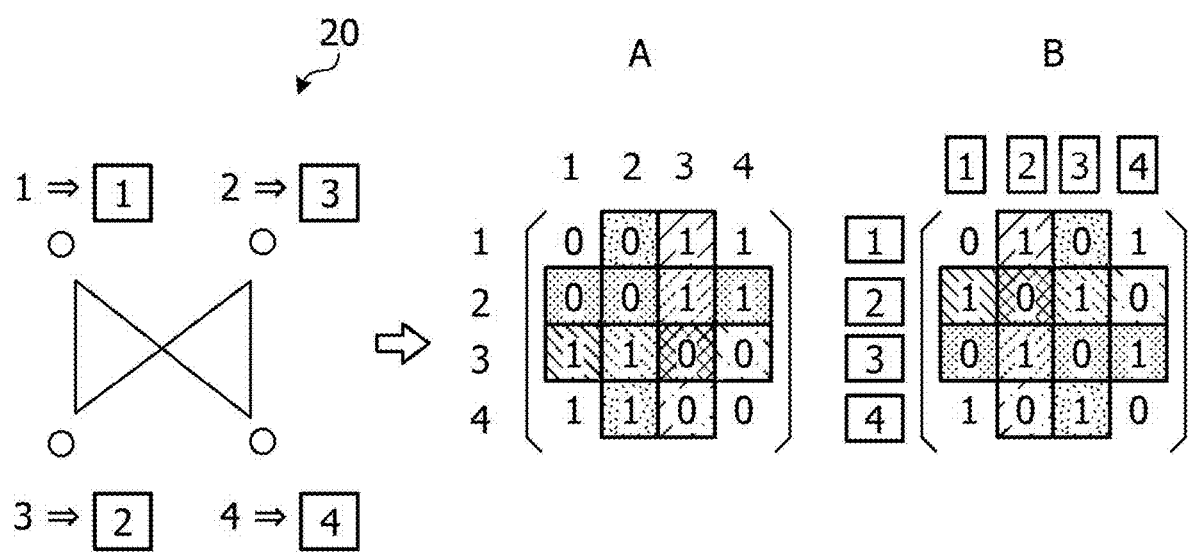
FIG. 6 is a diagram illustrating an example of a relationship between a graph structure and a tensor.

Next, a graph structure will be described with reference to FIGS. 6 and 7. FIG. 6 is a diagram illustrating an example of a relationship between a graph structure and a tensor. In a graph 20 illustrated in FIG. 6, four nodes are connected by edges indicating a relationship between the nodes (e.g., "correlation coefficient equal to or larger than a predetermined value"). There is no such relationship between nodes that are not connected by an edge. When the graph 20 is represented by a second order tensor, that is, a matrix, for example, a matrix representation based on a number on the left side of the node is represented by "matrix A". Meanwhile, a matrix representation based on a number on the right side of the node (a number surrounded by an enclosing line) is represented by "matrix B". Each element of these matrices is represented by "1" when nodes are coupled (connected) and by "0" when nodes are not coupled (not connected).

In the following description, such a matrix is also called a connection matrix. Here, the "matrix B" may be generated by simultaneously replacing the second and third rows and the second and third columns of the "matrix A". The deep tensor performs a process without regard to a difference in the arrangement order by using such a replacement process. That is, the "matrix A" and the "matrix B" are treated as the same graph in the deep tensor without regard to the arrangement order. The same process is executed for third or higher order tensors.

Figure 7:
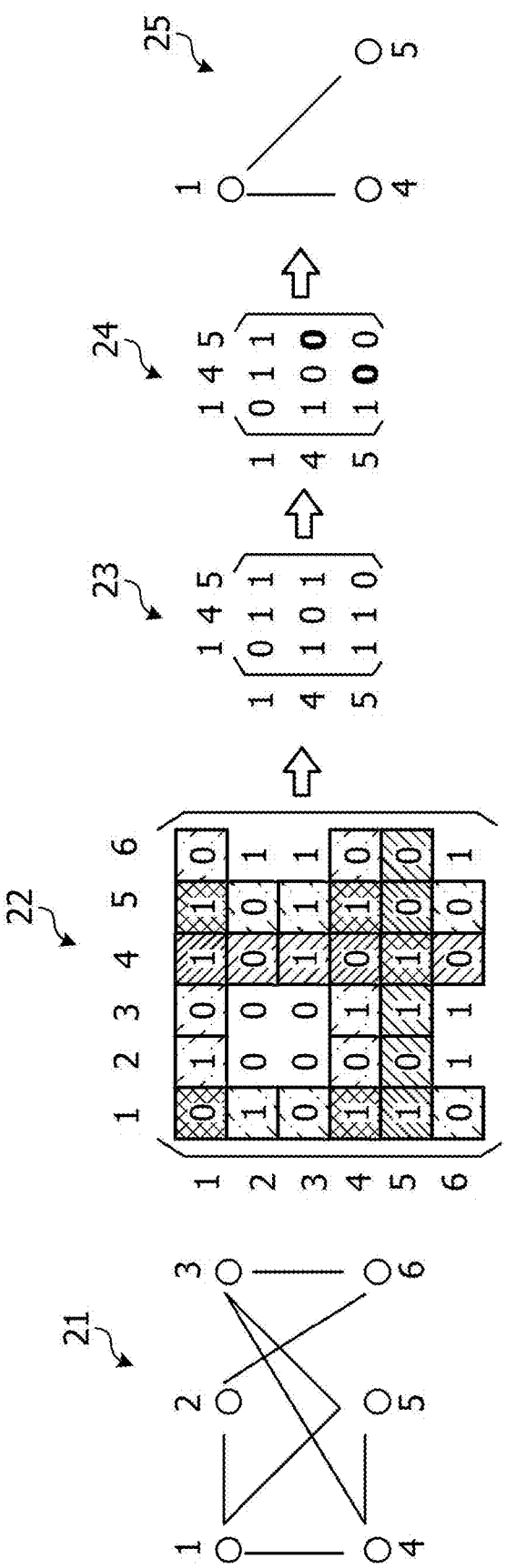
FIG. 7 is a diagram illustrating an example of extraction of a sub graph structure.

FIG. 7 is a diagram illustrating an example of extraction of a sub graph structure. In a graph 21 illustrated in FIG. 7, six nodes are connected by edges. When expressed by a matrix (tensor), the graph 21 may be represented as a matrix 22. A sub graph structure may be extracted by combining the matrix 22 with an operation of exchanging specific rows and columns, an operation of extracting specific rows and columns, and an operation of replacing nonzero elements in the connection matrix with zeros. For example, when a matrix corresponding to "node 1, 4, 5" of the matrix 22 is extracted, a matrix 23 is obtained. Next, when a value between "nods 4 and 5" of the matrix 23 are replaced with zero, a matrix 24 is obtained. The sub graph structure corresponding to the matrix 24 becomes a graph 25.

The extraction process of such sub graph structure is implemented by a mathematical operation called tensor decomposition. The tensor decomposition is an operation of approximating an input n-th order tensor by a product of n-th and lower order tensors. For example, the input n-th order tensor is approximated by a product of one n-th order tensor (called a core tensor) and n lower order tensors (when n≥2, usually a second order tensor, that is, a matrix, is used). This decomposition is not unique and any sub graph structure in the graph structure represented by the input data may be included in the core tensor.

The attendance record data may form graph data composed of a plurality of nodes and edges connecting the plurality of nodes. Here, the plurality of nodes is composed of nodes of date, month, and attendance category. There are as many date, month, and attendance category nodes as the number of dates, months, and attendance categories. Values corresponding to situations of date, month, and attendance category are stored in each node. For example, a value of "1" is set when the date is 1, a value of "2" is set when the attendance category is "day off", and a value of "1" is set when the attendance category is "attendance". The edge connects related nodes among the date node, the monthly node, and the attendance category node.

Figure 8:
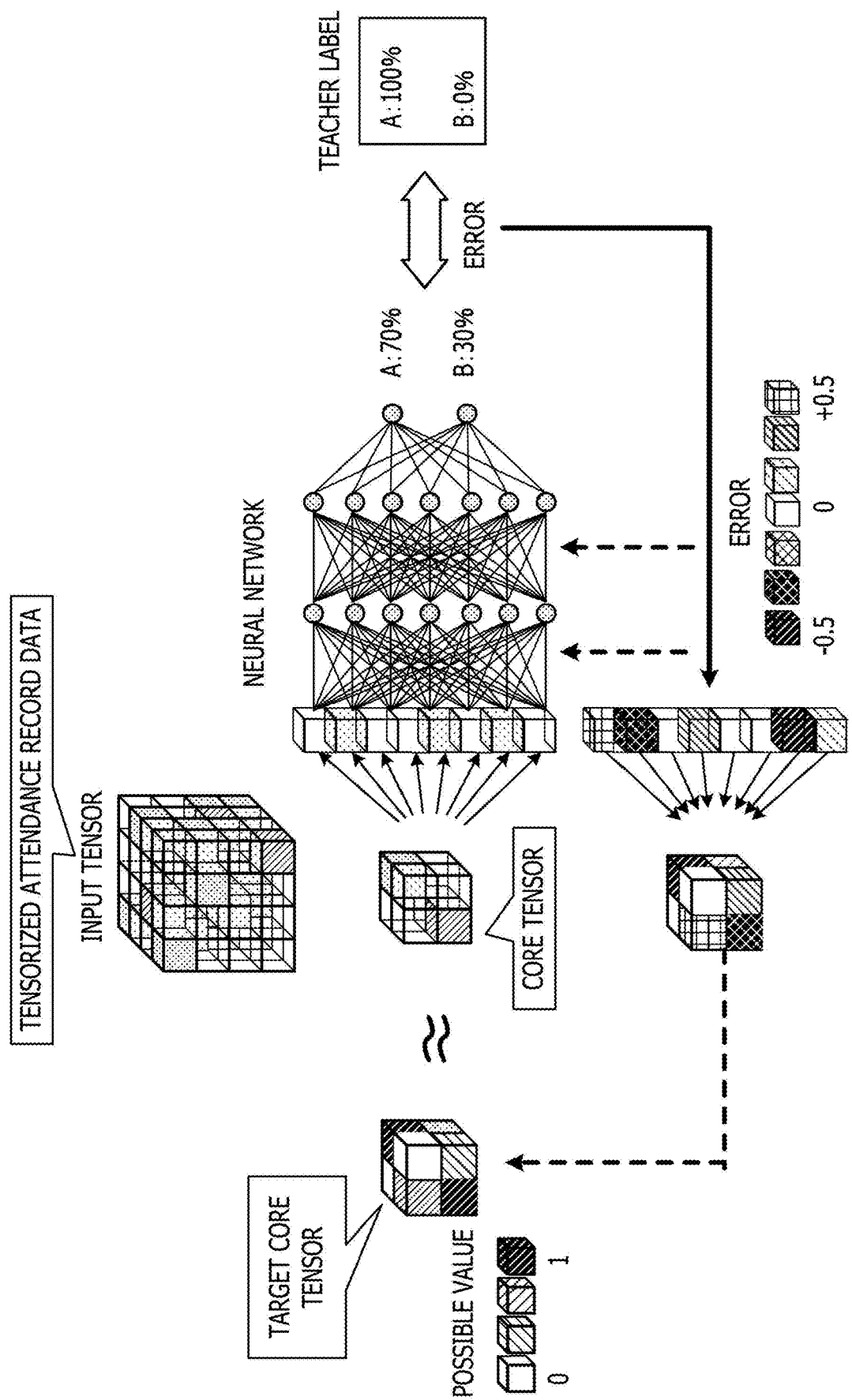
FIG. 8 is a diagram for explaining a learning example of a deep tensor.

Subsequently, learning of the deep tensor will be described. FIG. 8 is a diagram for explaining an example of learning of the deep tensor. As illustrated in FIG. 8, the information processing apparatus 100 generates an input tensor from attendance record data to which a teacher label (label A) such as "with recuperation" is attached. Then, the information processing apparatus 100 performs tensor decomposition on the input tensor and generates a core tensor similar to a target core tensor randomly generated at the first time. Then, the information processing apparatus 100 inputs the core tensor to the NN and obtains a classification result (label A: 70%, label B: 30%). After that, the information processing apparatus 100 calculates a classification error between a classification result (label A: 70%, label B: 30%) and a teacher label (label A: 100%, label B: 0%).

Here, the information processing apparatus 100 executes training of the prediction model and training of the tensor decomposition method by using an extended error back propagation method which is an extension of the error back propagation method. That is, the information processing apparatus 100 corrects various parameters of the NN such that the classification error is reduced in a manner to propagate the classification error to the lower layer in an input layer, an intermediate layer, and an output layer of the NN. Further, the information processing apparatus 100 propagates the classification error to the target core tensor and corrects the target core tensor so as to approach a partial structure of the graph that contributes to the prediction, that is, a feature pattern indicating a feature of a person with poor physical condition or a feature pattern indicating a feature of a normal person.

At the time of prediction after training, the prediction result may be obtained by converting an input tensor into a core tensor (partial pattern of the input tensor) by the tensor decomposition, so as to resemble the target core tensor, and inputting the core tensor to the neural network.

[Functional Configuration]

Figure 9:
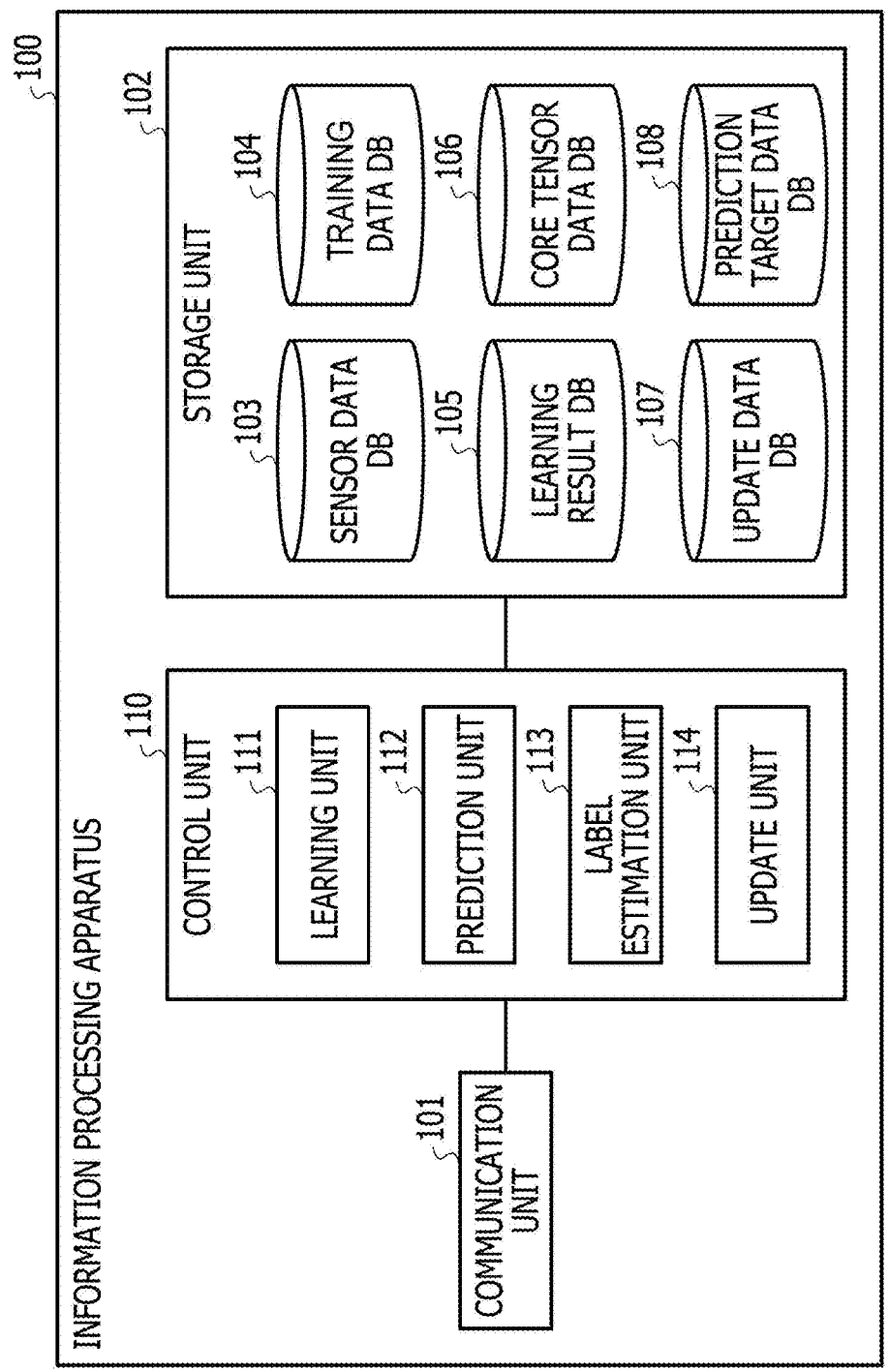
FIG. 9 is a diagram illustrating the functional configuration of an information processing apparatus according to a second embodiment.

FIG. 9 is a diagram illustrating the functional configuration of the information processing apparatus 100 according to the second embodiment. As illustrated in FIG. 9, the information processing apparatus 100 includes a communication unit 101, a storage unit 102, and a control unit 110.

The communication unit 101 is a processing unit that controls communication with other devices, and is, for example, a communication interface. For example, the communication unit 101 receives a processing start instruction, training data, an input tensor in which the training data is tensorized, and the like. The communication unit 101 also outputs learning results, prediction results, and the like.

The storage unit 102 is implemented by a storage device that stores programs and data (e.g., a memory or a hard disk). The storage unit 102 stores a sensor data DB 103, a training data DB 104, a prediction target data DB 108, a core tensor data DB 106, an update data DB 107, and a learning result DB 105.

The sensor data DB 103 is a database in which attendance record data related to attendance of employees and the like is stored. The attendance record data stored here is data of an attendance record used in each company, and may be acquired from various, known attendance management systems.

FIG. 10 is a diagram illustrating an example of information stored in the sensor data DB 103. As illustrated in FIG. 10, in the sensor data DB 103, "employee No.", "date", "day of the week", "attendance category", "attendance time", "leaving time", "overtime hours", and "business trip" are stored in association with each other. The types of attendance, recuperation, day off, etc. are stored in the "attendance category". The date and the day of the week are examples of elements that compose the attendance record data.

The example of FIG. 10 illustrates attendance record data of employee No. 100. For example, the second row in FIG. 10 is attendance record data for "Thursday, Apr. 2, 2015" and illustrates an example in which there is no business trip on that day, he/she comes to work at "8:49" and leaves at "0:00", and overtime time is "360 minutes". As another example, the seventh row in FIG. 10 is attendance record data for "Wednesday, Aug. 24, 2015" and illustrates an example in which the employee recuperates from this day to "Tuesday, Oct. 1, 2016". The attendance record data unit is not limited to each day, but may be a weekly unit or a monthly unit.

Referring back to FIG. 9, the training data DB 104 is a database in which information about training data to be tensorized is stored. Specifically, the training data DB 104 is data used for training of a learning model, and stores each training data that is a set of data obtained by cutting out the attendance record data in a period of 6 months and a teacher label.

For example, when the attendance record data of 6 months is used as one training data, and when there is a recuperation period within 3 months after that, "with recuperation" is set as a teacher label. When there is no recuperation period within 3 months after that, "without recuperation" is set as a teacher label. A teacher label "with recuperation" may be described as a "positive example" and a teacher label "without recuperation" may be described as a "negative example". When the attendance record data of 6 months includes a recuperation period, the data may not be adopted as training data. This is because it may be known that an employee who already has "recuperation" in the attendance record data of 6 months, which is the data (input) of the prediction source at the time of prediction, has recuperated most recently, and he/she will not be the target of recuperation prediction for 3 months.

FIG. 11 is a diagram illustrating an example of information stored in the training data DB 104. As illustrated in FIG. 11, the training data DB 104 stores information about "employee", "data ID", "data (explanatory variable)", and "teacher label (objective variable)" in association with each other. The "employee" stored here is an identifier that identifies an employee, and the "data ID" is an identifier that identifies training data. This data ID is information common to the DBs, and data in the DBs may be associated with this data ID. The "data (explanatory variable)" is data to be learned, and the "teacher label (objective variable)" is information to be an objective variable at the time of learning.

In the example of FIG. 11, in the attendance record data of the first employee (Taro Yamada) from January to June, "001" is set as the data ID and "with recuperation" is set as the "teacher label (objective variable)". In addition, in the attendance record data of the first employee from February to July, "002" is set as the data ID and "without recuperation" is set as the teacher label. In addition, in the attendance record data of the second employee (Jane Suzuki) from January to June, "011" is set as the data ID and "without recuperation" is set as the teacher label. Further, in the attendance record data of the second employee from February to July, "012" is set as the data ID and "without recuperation" is set as the teacher label.

Figure 12A:
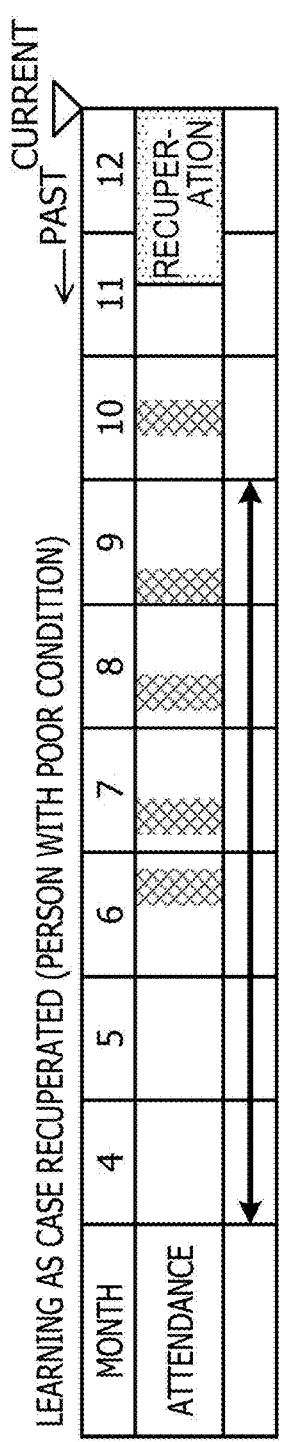
FIGS. 12A and 12B are diagrams for explaining an example of training data.
Figure 12B:
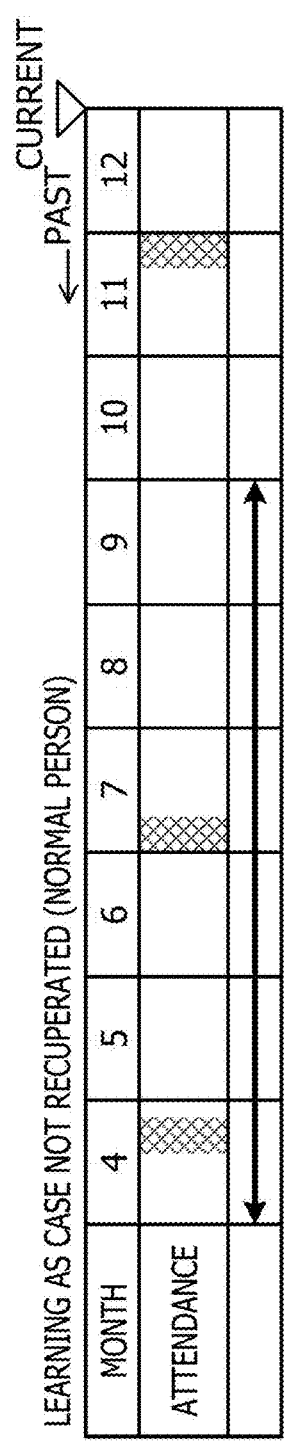

FIGS. 12A and 12B are diagrams for explaining an example of training data. Here, a setting example of the teacher label will be described in detail. The training data is composed of attendance record data every 6 months and a label indicating whether there is a recuperation record within 3 months after the 6 months. FIG. 12A illustrates attendance record data of a person with poor physical condition to whom a label "with recuperation" is attached. FIG. 12B illustrates attendance record data of a normal person to whom a label "without recuperation", which indicates the person has not recuperated, is attached. As illustrated in FIGS. 12A and 12B, the information processing apparatus 100 according to the second embodiment trains a prediction model with "attendance record data of 6 months, label (with recuperation)" and "attendance record data of 6 months, label (without recuperation)" as the training data. After the training, the information processing apparatus 100 predicts whether or not a person recuperates within 3 months from the attendance record data of 6 months. A shaded area in FIGS. 12A and 12B indicates day off.

Referring back to FIG. 9, the prediction target data DB 108 is a database that stores information about prediction target data for which whether or not the employee recuperates is predicted using a trained learning model. In the prediction target data DB 108, "year", "data ID", "employee", and "data" are stored in association with each other.

The "year" stored here indicates the year of the attendance record data of a prediction target, and the "data ID" is an identifier for identifying prediction target data. The "employee" is an identifier of an employee for whom the possibility of recuperation is predicted, and the "data" is data to be input to the learning model.

The core tensor data DB 106 is a database in which information about core tensors acquired at each stage is stored. Specifically, the core tensor data DB 106 stores data of core tensors acquired at each stage, such as a core tensor at learning, a core tensor at prediction, and a core tensor at update.

FIG. 13 is a diagram illustrating an example of information stored in the core tensor data DB 106. As illustrated in FIG. 13, in the core tensor data DB 106, "core tensor at learning", "core tensor at prediction", and "core tensor at update" are stored in association with each other for each of a plurality of data IDs. As illustrated in FIG. 13, core tensor data is stored in the corresponding core tensor column, and "-" or the like is set in the non-applicable column. The example of FIG. 13 illustrates that "core tensor X" is generated as "core tensor at learning" from training data to which the data ID "X" is assigned.

The "core tensor at learning" indicates core tensor data generated from the training data at the time of training a learning model. The "core tensor at prediction" indicates core tensor data generated from the prediction target data at the time of prediction using the trained learning model. The "core tensor at update" indicates core tensor data generated, using the trained learning model to be updated, from attendance record data at the time when it is possible to determine whether the prediction at the time of prediction is correct or incorrect.

Referring back to FIG. 9, the update data DB 107 is a database that stores information about training data for update, which is used to update a trained learning model. That is, the update data DB 107 stores training data for retraining, which is generated by the control unit 110 to be described later. In the update data DB 107, "data ID", "data", and "teacher label" are stored in association with each other. The "data ID" stored here is an identifier for identifying training data for update. The "data" is attendance record data that serves as an explanatory variable at the time of updating. The "teacher label" is attendance record data that serves as an objective variable at the time of updating.

The learning result DB 105 is a database in which information about learning results is stored. For example, the learning result DB 105 stores a discrimination result (classification result) of the training data by the control unit 110, various parameters of a deep tensor, various parameters of the NN, and the like, that are learned by machine learning or deep learning. The learning result DB 105 may store a trained learning model itself in which various parameters optimized by learning are set.

The control unit 110 is a processing unit that controls the entire processing of the information processing apparatus 100, and is, for example, a processor or the like. The control unit 110 includes a learning unit 111, a prediction unit 112, a label estimation unit 113, and an update unit 114. The learning unit 111, the prediction unit 112, the label estimation unit 113, and the update unit 114 are examples of an electronic circuit included in a processor or the like, or examples of a process executed by the processor or the like.

The learning unit 111 is a processing unit that executes training of a learning model to which a neural network is applied, by deep learning using the deep tensor described in FIG. 8. Specifically, the learning unit 111 reads each training data stored in the training data DB 104, and executes training of the learning model taking the data of each training data as an explanatory variable and taking the teacher label as an objective variable. Then, when the training is completed, the learning unit 111 stores the parameters of the optimized neural network in the learning result DB 105 as the learning result. When the training is completed, the learning unit 111 may store the trained learning model itself in which the parameters of the optimized neural network are set, in the learning result DB 105 as the learning result.

Here, when the training data is input to the learning model (NN), the learning unit 111 generates and inputs tensor data obtained by tensorizing the training data to execute a learning process that uses the deep tensor.

Figure 14:
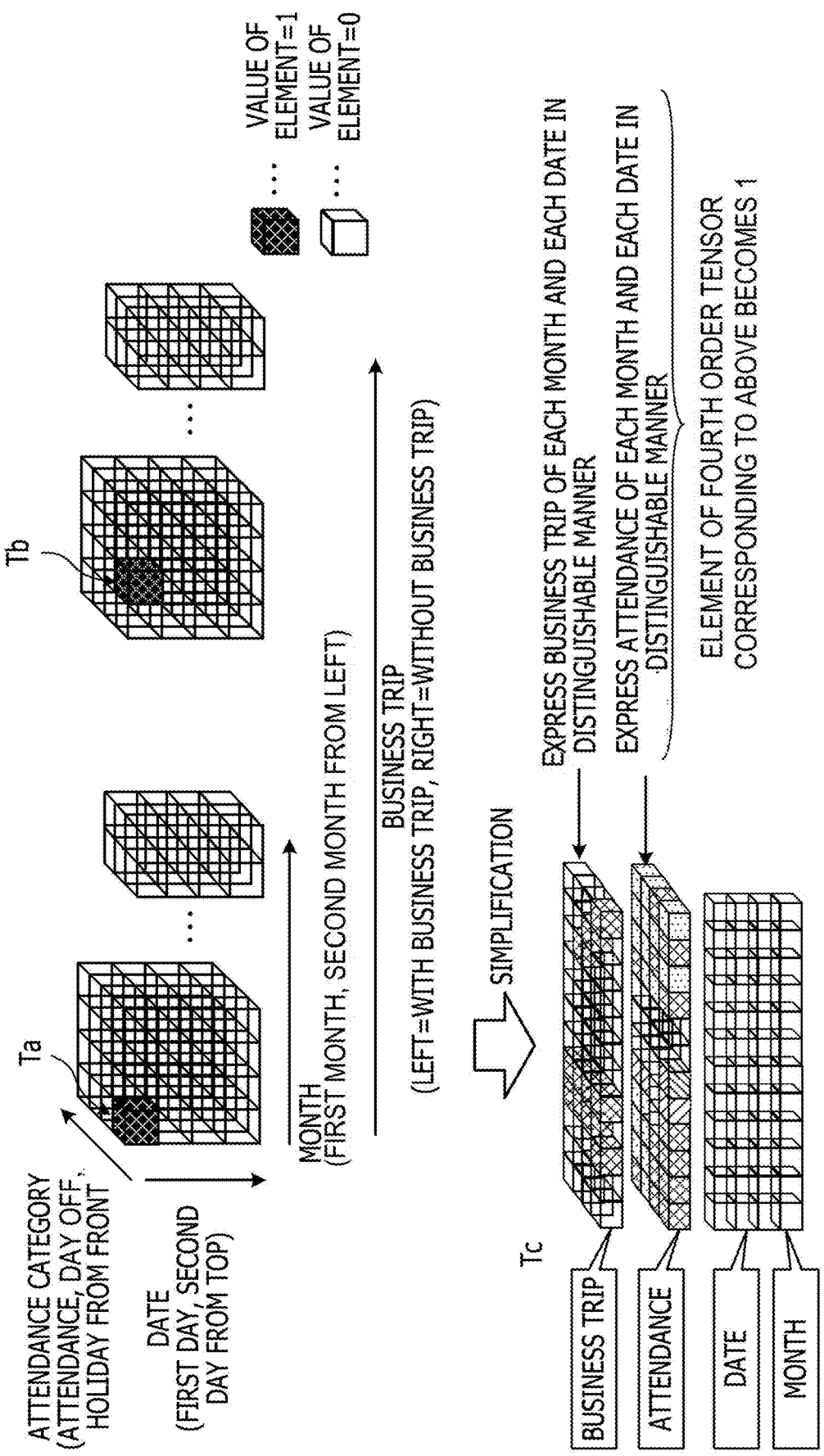
FIG. 14 is a diagram for explaining tensorization.

FIG. 14 is a diagram for explaining the tensorization. As illustrated in FIG. 14, a tensor generated by the learning unit 111 indicates data of "month" in the horizontal direction, "date" in the vertical direction, "attendance category" in the depth direction, "with business trip" in the left, and "without business trip" in the right. The "date" indicates days in order with the first day at the top, and the "attendance category" indicates attendance, day off, and holiday from the front. For example, in FIG. 14, the symbol "Ta" indicates an element of attendance and making a business trip on the first day of the first month, and the symbol "Tb" indicates an element of taking a day off and not making a business trip on the first day of the second month. In the present embodiment, the tensor described above may be simplified and described as "Tc" in FIG. 14. In other words, the tensor is represented as a cubic shape that overlaps elements of month, date, attendance category, and presence/absence of business trip. The presence or absence of business trip of each month and date is represented separately, and the attendance category of each month and date is also represented separately.

Referring back to FIG. 9, the learning unit 111 acquires a core tensor generated by tensor decomposition for each training data at the time of learning based on each training data. Then, the learning unit 111 stores each acquired core tensor in the core tensor data DB 106 in association with the training data ID. That is, the learning unit 111 acquires the "core tensor at learning" for each training data.

For example, the learning unit 111 reads training data (data, teacher label (without recuperation)) of data ID "4" from the training data DB 104, and inputs data "attendance record data from January to June" as an explanatory variable to the NN. Subsequently, the learning unit 111 executes training of the NN such that an error between an output result of the NN and a teacher label of "without recuperation" becomes smaller. Further, the learning unit 111 acquires a core tensor A generated from the data "attendance record data from January to June" at the time of learning, and stores the core tensor A in the core tensor data DB 106.

The prediction unit 112 is a processing unit that uses a trained learning model to predict whether each employee is at high risk of recuperation. Specifically, when training of the learning model is completed, the prediction unit 112 acquires parameters and the like from the learning result DB 105 and builds a trained learning model. Then, the prediction unit 112 reads prediction target data from the prediction target data DB 108, tensorizes the prediction target data in the same way as learning and inputs such data into the trained learning model, predicts the possibility of recuperation based on the output result, and stores the prediction result in the storage unit 102 or outputs the prediction result to the display unit 203.

The prediction unit 112 also acquires a core tensor generated by tensor decomposition or the like for each prediction target data at the time of prediction based on each prediction target data. Then, the prediction unit 112 stores each acquired core tensor in the core tensor data DB 106 in association with the ID of the prediction target data. That is, the prediction unit 112 acquires the "core tensor at prediction" for each prediction target data.

For example, the prediction unit 112 reads prediction target data of a data ID "PPP" from the prediction target data DB 108, and inputs data "attendance record data from June to December 2019" to a trained learning model (NN). Subsequently, the prediction unit 112 acquires the probability of being a positive example (with recuperation) and the probability of being a negative example (without recuperation) as an output result of the trained learning model. Then, the prediction unit 112 determines the higher probability among the respective probabilities as a prediction result. Further, the prediction unit 112 acquires a core tensor PPP generated from the data "attendance record data from June to December 2019" at the time of prediction, and stores the core tensor PPP in the core tensor data DB 106. The prediction unit 112 may acquire and retain a core tensor only for the prediction target data whose prediction result is a "positive example (with recuperation)".

The label estimation unit 113 is a processing unit that estimates a teacher label to be assigned to new training data based on a change in the core tensor at prediction and the core tensor at update. Specifically, the label estimation unit 113 calculates a similarity between the core tensor at prediction and the core tensor at learning for attendance record data of a certain employee. The label estimation unit 113 also calculates a similarity between the current core tensor, which is at update timing, and the core tensor at learning. Then, the label estimation unit 113 assigns a teacher label based on comparison between the similarities to the new training data and stores the assigned teacher label in the update data DB 107.

Figure 15:
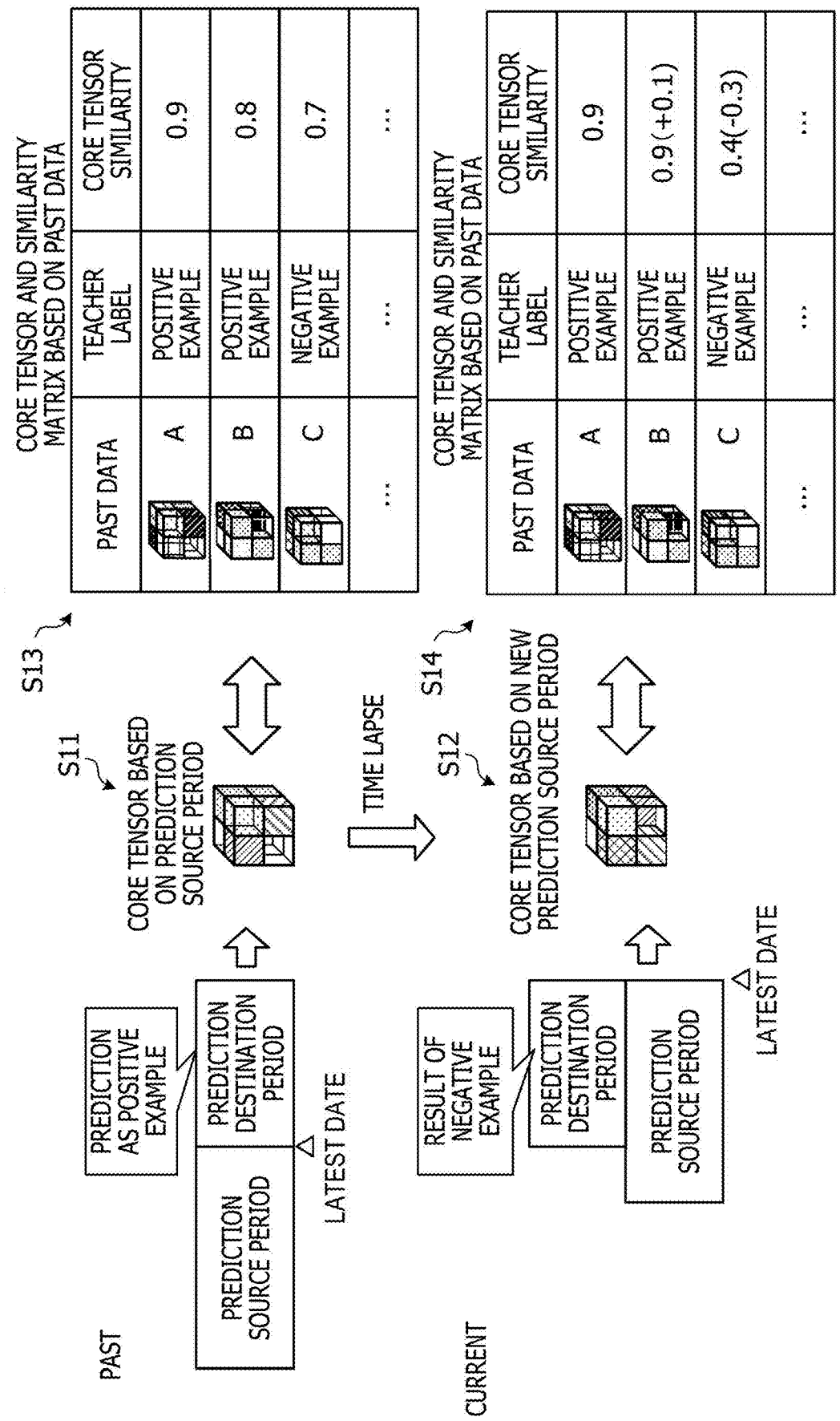
FIG. 15 is a diagram for explaining similarity calculation and teacher label estimation.

FIG. 15 is a diagram for explaining similarity calculation and teacher label estimation. For example, attendance record data of an employee X will be described as an example. As illustrated in FIG. 15, at the time of prediction (in the past), the prediction unit 112 uses data of a prediction source period, which is the attendance record data of the employee X from the latest date to 6 months before to predict whether the employee X will recuperate in a prediction destination period from the latest date to 3 months after. At this time, the prediction unit 112 acquires a core tensor based on data of the prediction source period (S11).

Referring back to FIG. 9, the prediction unit 112 predicts a "positive example", that is, "in recuperation", and when the current date and time passes predicted time, refers to the attendance record data of each employee to determine whether or not the prediction is correct. Here, it is assumed that after the elapse of the prediction destination period, the employee X may come to work as usual without "recuperation". In this case, the correct answer is a "negative example" even when it is a "positive example" at the time of prediction. In this case, it is common that a teacher label of "negative example" is assigned to newly generated training data. However, it is not possible to determine whether the prediction is incorrect or whether the correct answer is changed due to a predetermined action on the employee X. Therefore, when the teacher label is assigned as it is, the reliability becomes lower.

Then, the label estimation unit 113 generates a core tensor based on data of a new prediction source period, which is the attendance record data from the current latest date after the lapse of the prediction destination period to six months before, among the attendance record data of the employee X whose result is changed to a "negative example" instead of a "positive example" (S12).

Subsequently, the label estimation unit 113 uses a method such as cosine similarity, k-means clustering, or the like to calculate the similarity between the core tensor based on the prediction source period at the time of prediction and the core tensor (core tensor at the time of learning) generated from each training data (S13).

For example, the label estimation unit 113 calculates the similarity of "0.9" between the core tensor at the time of prediction and the core tensor A based on the training data A to which the teacher label of "positive example" is assigned. Similarly, the label estimation unit 113 calculates the similarity of "0.8" between the core tensor at the time of prediction and the core tensor B based on the training data B to which the teacher label of "positive example" is assigned, and the similarity of "0.7" between the core tensor at the time of prediction and the core tensor C based on the training data C to which the teacher label of "negative example" is assigned.

Subsequently, the label estimation unit 113 uses a method such as a cosine similarity, k-means clustering, or the like to calculate the similarity between the core tensor based on the new prediction source period at the time of update and the core tensor at the time of each learning (S14).

For example, the label estimation unit 113 calculates the similarity of "0.9" between the core tensor at the time of update and the core tensor A based on the training data A to which the teacher label of "positive example" is assigned. Similarly, the label estimation unit 113 calculates the similarity of "0.9" between the core tensor at the time of update and the core tensor B based on the training data B to which the teacher label of "positive example" is assigned, and the similarity of "0.4" between the core tensor at the time of update and the core tensor C based on the training data C to which the teacher label of "negative example" is assigned.

After that, the label estimation unit 113 calculates a difference in similarity from the time of update to the time of prediction to determine whether a change to a positive example or a negative example has occurred. Then, the label estimation unit 113 determines a teacher label to be assigned to the data of the new prediction source period based on a result of the determination.

Specifically, the label estimation unit 113 calculates a change in similarity by converting based on the negative example. For example, the label estimation unit 113 calculates a difference for a change in "positive example group" by "similarity at prediction-similarity at update". The label estimation unit 113 calculates a difference for a change in "negative example group" by "similarity at update-similarity at prediction".

In the example of FIG. 15, for the "positive example group", the label estimation unit 113 calculates a difference of "0.9−0.9=0" in similarity with respect to the core tensor A and calculates a difference of "0.8−0.9=−0.1" in similarity with respect to the core tensor B. Further, the label estimation unit 113 calculates a difference of "0.4−0.7=−0.3" in similarity with respect to the core tensor C for the "negative example group". Then, since the total value of "0+(−0.1)+(−0.3)=−0.4" of the differences is smaller than a threshold value (e.g., 0.1), the label estimation unit 113 determines that the core tensor at the time of update is moving away from the negative example (close to the positive example). As a result, the label estimation unit 113 generates training data for update in which the teacher label to be assigned to the data of the new prediction source period is not the actual result of "negative example" but the estimation result of "positive example".

The comparison of similarities may be performed by various methods. For example, the label estimation unit 113 may adopt a teacher label with the larger variation from among the variation of the similarity with the training data whose teacher label is a "positive example" and the variation of the similarity with the training data whose teacher label is a "negative example". In the example of FIG. 15, the label estimation unit 113 calculates "0+0.1=0.1" as the variation of the positive example and "−0.3" as the variation of the negative example, and adopts the "positive example" with a larger value.

Further, when the certainty of a change from the positive example to the negative example is determined, the similarity with the "negative example" in the training data may be calculated. When a change in the similarity is equal to or larger than a threshold value, the "negative example" may be selected. When the change in the similarity is smaller than the threshold value, the "positive example" may be selected.

Referring back to FIG. 9, the update unit 114 is a processing unit that uses the training data for update stored in the update data DB 107 to update the trained learning model in the same manner as at the time of learning. That is, the update unit 114 re-trains the trained learning model.

For example, the update unit 114 reads the training data (data, teacher label (with recuperation)) of the data ID "PPP" from the update data DB 107, and inputs the data "attendance record data from June to December 2019" to the trained learning model (NN). Subsequently, the update unit 114 executes training of the learning model such that an error between the output result of the learning model and the teacher label of "with recuperation" becomes smaller.

When the re-training is completed, the update unit 114 stores the parameters of the optimized neural network or the learning model in which the parameters of the optimized neural network are set, in the learning result DB 105 as a learning result.

[Flow of Process]

Figure 16:
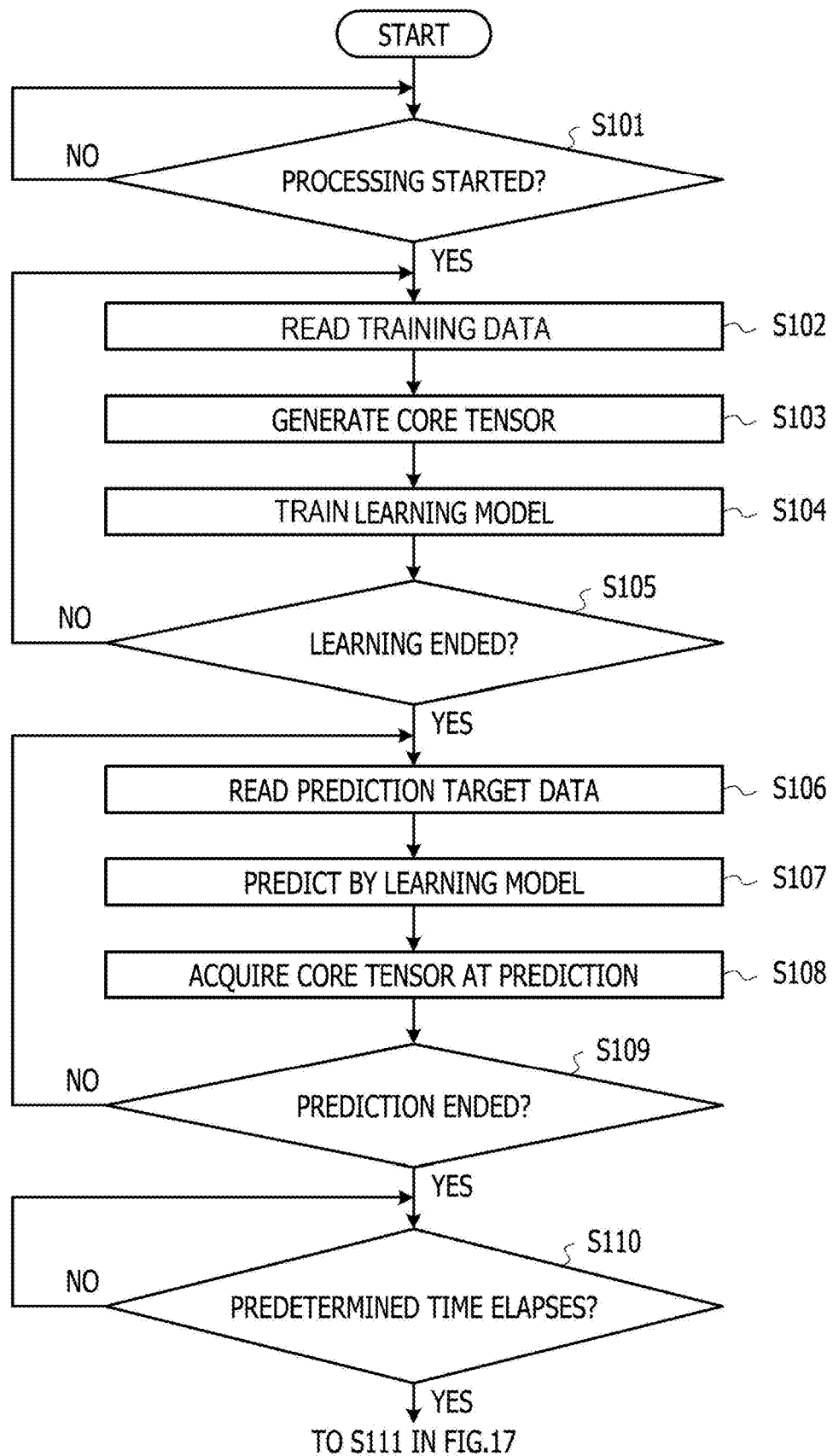
FIG. 16 is a flowchart illustrating a flow of a process of the second embodiment.
Figure 17:
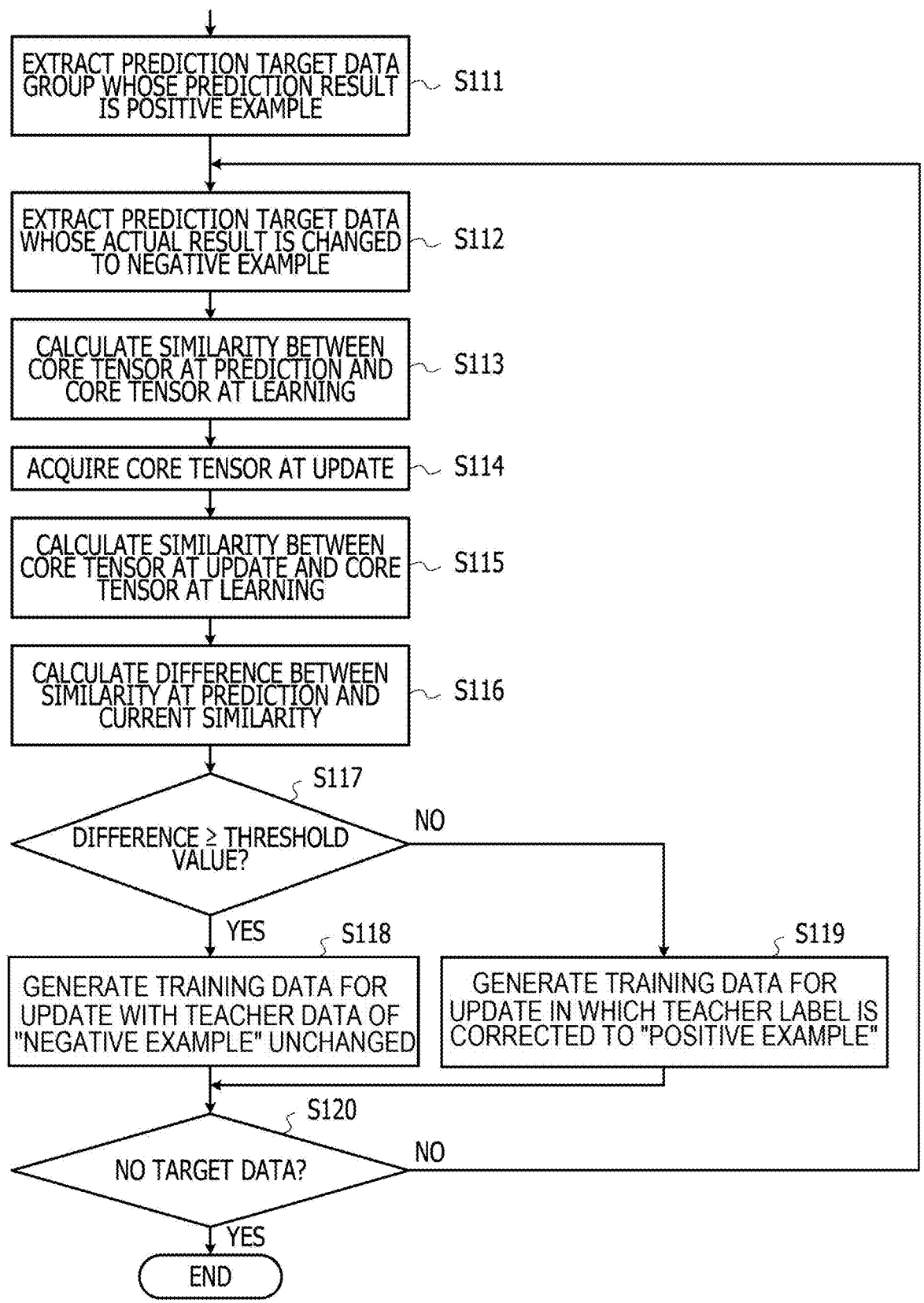
FIG. 17 is a flowchart illustrating a flow of a process of the second embodiment.

FIGS. 16 and 17 are flowcharts illustrating a flow of a process. As illustrated in FIGS. 16 and 17, S101 is repeated until the start of a process is instructed ("No" in S101). When the start of the process is instructed ("Yes" in S101), the learning unit 111 reads training data (S102), generates and stores a core tensor (S103), and performs training of a learning model using the core tensor (S104).

Then, the learning unit 111 repeats S102 and subsequent steps until the learning is completed ("No" in S105). Meanwhile, as illustrated in FIG. 16, when the learning is completed ("Yes" in S105), the prediction unit 112 reads prediction target data (S106), executes tensorization and the like by the same method as the learning, and executes prediction by using the trained learning model (S107). Further, the prediction unit 112 acquires and stores a core tensor at prediction generated at the time of prediction (S108).

In addition, the prediction unit 112 repeats S106 and subsequent steps until there is no prediction target data ("No" in S109). Meanwhile, as illustrated in FIG. 16, when the prediction for all the prediction target data is completed ("Yes" in S109), S110 is repeated until a predetermined period elapses ("No" in S110). When the predetermined period elapses ("Yes" in S110), the label estimation unit 113 extracts a prediction target data group whose prediction result is a "positive example" (S111), and extracts prediction target data whose actual result is changed to a "negative example" (S112).

Then, the label estimation unit 113 calculates the similarity between the core tensor at the time of prediction of the extracted prediction target data and the core tensor at the time of learning of each training data (S113).

Further, the label estimation unit 113 acquires a core tensor (the core tensor at update) based on the current attendance record data of an employee whose prediction result is changed (S114), and calculates the similarity between the core tensor at update and the core tensor at learning of each training data (S115). After that, the label estimation unit 113 calculates a difference between the similarity at prediction and the similarity at the present time (at update) (S116).

Then, when the difference is equal to or larger than a threshold value ("Yes" in S117), the label estimation unit 113 does not correct the teacher label as "negative example" and generates training data for update of "negative example" (S118). Meanwhile, when the difference is smaller than the threshold value ("No" in S117), the label estimation unit 113 corrects the teacher label from "negative example" to "positive example" and generates training data for update of "positive example" (S119).

When there is no target data ("Yes" in S120), the label estimation unit 113 ends the process. Meanwhile, when there is any target data ("No" in S120), the process proceeds to S112.

[Effects]

As described above, the information processing apparatus 100 may maintain the learning model accuracy by assigning the teacher label in consideration of the measure effect based on the prediction result and adopting such a label as new training data. The information processing apparatus 100 may maintain the accuracy of the learning model by preventing rare sample data (positive example) from being damaged due to imbalance of a prediction task.

Difference Between First Embodiment or Second Embodiment and Comparative Example Here, the effects of the first embodiment or the second embodiment will be specifically described using a comparative example. The information processing apparatus 100 illustrated in FIGS. 1A and 9 trains a learning model for predicting whether there is a possibility of recuperation within 3 months based on the attendance record data for 6 months by using each training data that takes the attendance record data of an employee for 6 months as an explanatory variable and takes a teacher label indicating "positive example" with recuperation experience or "negative example" without recuperation experience as an objective variable.

Then, when the learning is completed, the information processing apparatus 100 predicts whether there is a high risk of recuperation of the employee based on a result obtained by inputting the attendance record data of the employee, which is the prediction target to the trained learning model.

After that, the information processing apparatus 100 generates training data by newly assigning a result indicating whether or not the employee actually recuperates as a teacher label to the attendance record data of the employee, which is the prediction target, and updates the learning model using the training data. In this way, the information processing apparatus 100 may maintain the accuracy of prediction by the learning model by regularly updating the learning model.

Figure 18:
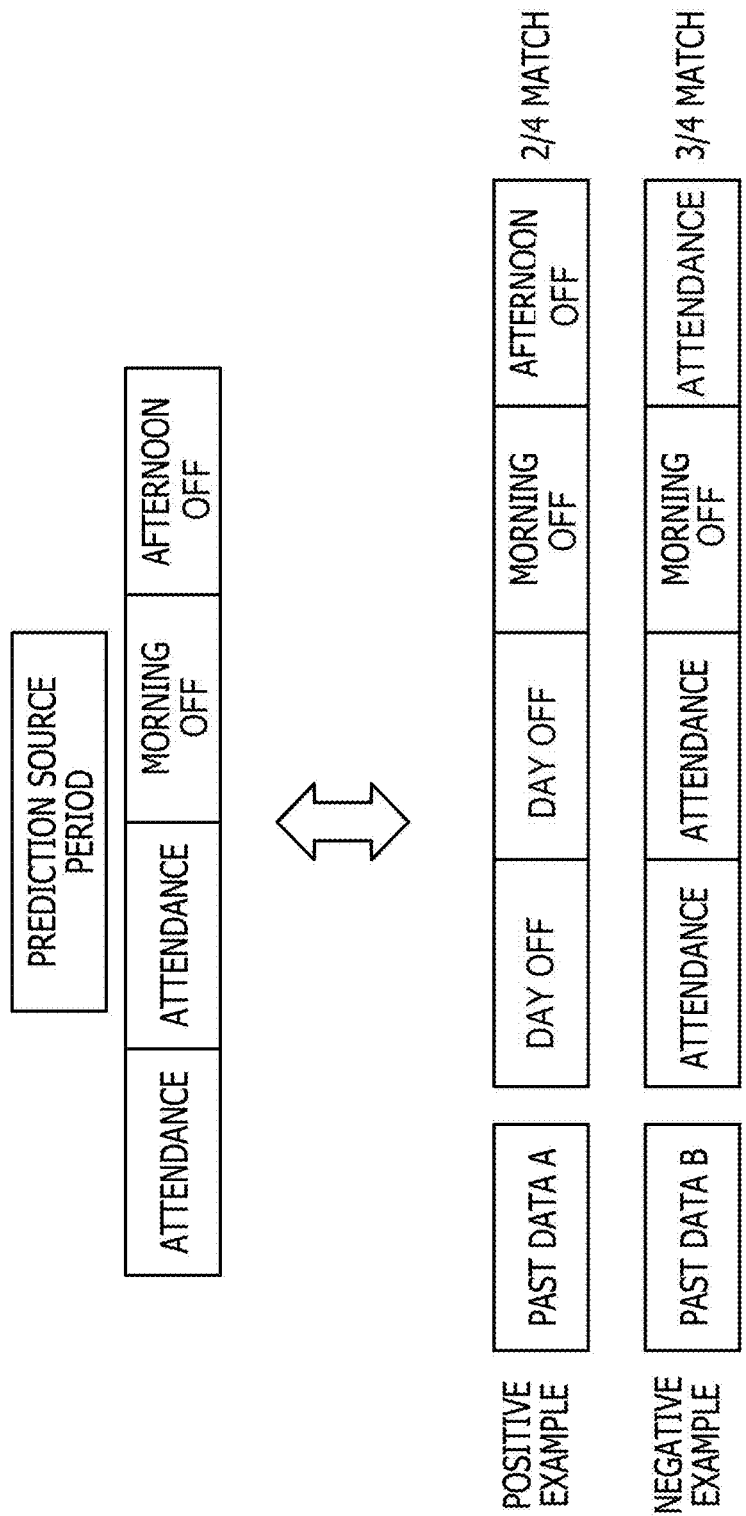
FIG. 18 is a diagram for explaining a problem of teacher label estimation according to a comparative example.

Subsequently, a process of the comparative example will be described with reference to FIG. 18. When "positive example" is predicted at the time of prediction, it is common that a measure to avoid recuperation is taken. Since a result of the measure may be "negative example" that is different from the prediction, assigning the actual result as a teacher label, as it is, may cause learning noise. Therefore, in general, training data for update of the learning model is generated by calculating the similarity between each training data whose teacher label is known and the prediction target data and assigning a teacher label of the training data with the highest similarity to the prediction target data. Here, the attendance record data of a certain employee will be described as an example. At the time of prediction (in the past), attendance record data A in the prediction source period, which is 6 months from the latest date at that time, is input to the trained learning model and acquires the prediction result of "positive example".

Then, it is assumed that an employee who is determined to be "positive example" is given counseling, etc., and even after 3 months (currently), the employee is able to go to work without recuperation. In this case, although it is originally predicted to be a positive example, it is unclear whether the negative example is due to a measure or is a negative example from the beginning (false prediction).

For this reason, in the comparative example, attendance record data B that is 6 months back from the current latest date is extracted as an explanatory variable, the similarity between the attendance record data and each training data (past data) used for learning is calculated, and a teacher label to be set is determined according to the calculated similarity.

For example, the similarity of "2/4" between the attendance record data B of "attendance, attendance, morning off, afternoon off" and the past data A of "day off, day off, morning off, afternoon off" to which the teacher label of "positive example" is set is calculated. Similarly, the similarity of "3/4" between the attendance record data B of "attendance, attendance, morning off, afternoon off" and the past data B of "attendance, attendance, morning off, attendance" to which the teacher label of "negative example" is set is calculated.

As a result, since the similarity with the past data B is higher, the training data for update in which the same teacher label of "negative example" as in the past data B is set to the attendance record data B of "attendance, attendance, morning off, afternoon off" is generated. In other words, in similarity evaluation between the attendance record data B and the past data, since it is close to the past data B of the negative example, the possibility of false detection increases as a result. Therefore, when adding as new training data, a negative example label is assigned as it is. In other words, it is estimated that the prediction is not correct, not the measure effect.

However, since such a simple similarity comparison uniquely compares data, there is a high possibility that it is estimated that a teacher label misses an important part in the original prediction task. FIG. 18 is a diagram for explaining a problem of the estimation of the teacher label according to the comparative example. As illustrated in FIG. 18, it is assumed that an important part that impairs health is a part where "morning off" and "afternoon off" are continuously connected. In this case, in a simple similarity comparison, it is evaluated that the attendance record data B is close to a negative example, but when focusing on the important part, it is natural that it be close to a positive example. Therefore, when it is adopted as a negative example sample for new training data, it becomes odd training data in which the measure effect is not taken into consideration, and the learning accuracy is deteriorated.

Third Embodiment

Although the embodiments of the present disclosure have been described so far, the present disclosure may be implemented in various different forms other than the above-described embodiments.

[Numerical Values, Etc.]

The data examples, numerical values, threshold values, the number of teacher labels, specific examples, etc. used in the above embodiments are merely examples and may be arbitrarily changed. Further, the input data, the learning method, etc. are merely examples and may be arbitrarily changed. Various models such as a neural network may be adopted as the learning model.

[Training Data for Update]

For example, in the above flowcharts and the like, descriptions have been made on an example in which the teacher label is corrected for the prediction target data that is predicted as "positive example" but actually becomes "negative example", but the present disclosure is not limited thereto. For example, the teacher label may be corrected for all the prediction target data. Further, the above process may be executed only for the prediction target data for which the prediction result and the actual result are different. Further, for the prediction target data for which the prediction result and the actual result are the same, it is possible to generate training data for update using the actual result as a teacher label, as it is. The actual result may be identified by attendance record data.

[Learning]

The learning process described above may be executed for any number of times. For example, it may be executed using all the training data, or may be executed a predetermined number of times. As a method of calculating the classification error, a known calculation method such as the least square method may be adopted, and a general calculation method used in NN may also be adopted. The training data and the attendance record data may also be acquired from an external device.

[Supposed System]

In the above-described embodiments, an example of learning the attendance record data and predicting an employee who is likely to recuperate has been described, but the present disclosure is not limited thereto. For example, the present disclosure may be applied to failure prediction using operation data of electronic components, attack prediction using communication data, traffic congestion prediction using road traffic data, and the like.

[Neural Network]

In the present embodiments, various neural networks such as RNN (Recurrent Neural Networks), CNN (Convolutional Neural Networks), and the like may be used. Further, as the learning method, various known methods other than the error back propagation method may be adopted. The neural network has a multi-stage structure including, for example, an input layer, an intermediate layers (hidden layers), and an output layer, and each layer has a structure in which a plurality of nodes are connected by edges. Each layer has a function called "activation function", the edge has "weight", and the value of each node is calculated from the value of a node of the previous layer, the weight value of a connection edge (weight coefficient), and the activation function of the layer. As the calculation method, various known methods may be adopted.

Moreover, learning in the neural network (training the neural network) is to modify parameters, that is, weights and biases, such that the output layer has a correct value. In the error back propagation method, a "loss function" that indicates how far the output layer value is from the correct state (desired state) is defined for the neural network, and the steepest descent method, etc. is used to update the weights and the biases such that the loss function is minimized.

[System]

The information including the processing procedures, control procedures, specific names, and various data and parameters illustrated in the above documents and drawings may be changed arbitrarily unless otherwise specified. The specific examples, distributions, numerical values, etc. described in the embodiments are merely examples and may be arbitrarily changed.

Each component of each device illustrated in the drawings is functionally conceptual, and does not necessarily have to be physically configured as illustrated. That is, the specific forms of distribution and integration of each device are not limited to those illustrated. That is, all or a part of such forms may be functionally or physically distributed/integrated in arbitrary units according to various loads and usage conditions. Furthermore, all or a part of each processing function performed in each device may be implemented by a central processing unit (CPU) and a program analyzed and executed by the CPU, or may be implemented as hardware by wired logic. For example, the learning process, the generation process of the training data for update, and the updating process may be implemented by different devices.

[Hardware]

Figure 19:
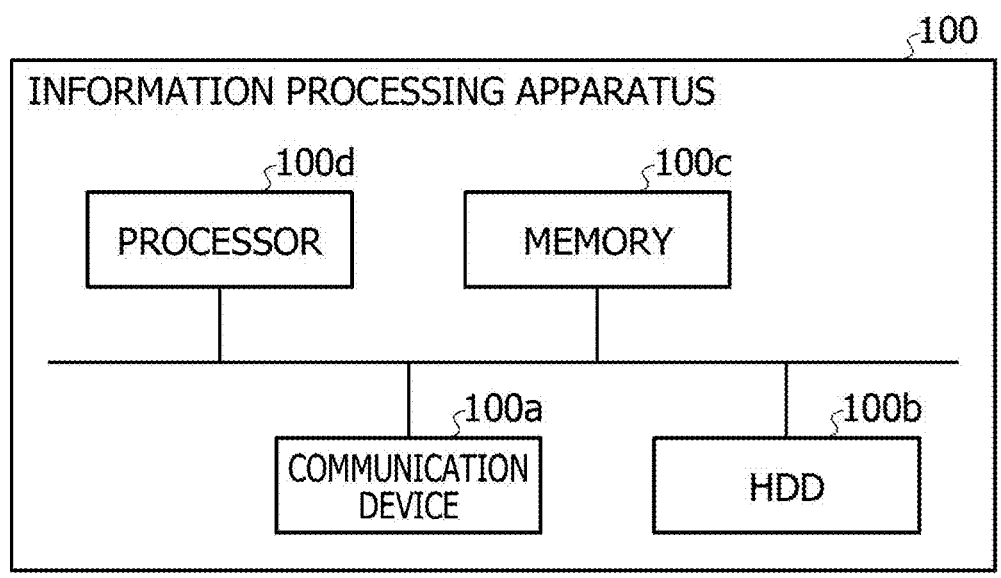
FIG. 19 is a diagram for explaining a hardware configuration example.

FIG. 19 is a diagram for explaining a hardware configuration example. As illustrated in FIG. 19, the information processing apparatus 100 includes a communication device 100a, a hard disk drive (HDD) 100b, a memory 100c, and a processor 100d. Further, the respective units illustrated in FIG. 19 are interconnected by a bus or the like.

The communication device 100a is a network interface card or the like, and communicates with other servers. The HDD 100b stores a program and DB for operating the functions illustrated in FIGS. 1A and 9.

The processor 100d operates a process that executes each function described with reference to FIG. 6, etc. by reading a program that executes the same process as each processing unit illustrated in FIGS. 1A and 9 from the HDD 100b or the like and deploying the program on the memory 100c. That is, this process executes the same function as each processing unit included in the information processing apparatus 100. Specifically, the processor 100d reads, from the HDD 100b or the like, a program having the same functions as the control unit 110, the learning unit 111, the prediction unit 112, the label estimation unit 113, the update unit 114, the first extraction unit 121, the second extraction unit 122, the determination unit 123, the execution unit 124, and the like. Then, the processor 100d executes a process that executes the same processing as the learning unit 111, the prediction unit 112, the label estimation unit 113, the update unit 114, and the like.

In this way, the information processing apparatus 100 operates as an information processing apparatus that executes a data generation method by reading and executing a program. Further, the information processing apparatus 100 may also implement the same functions as those of the above-described embodiments by reading the program from a recording medium by a medium reading device and executing the read program. A program referred to in the third embodiment is not limited to being executed by the information processing apparatus 100. For example, the present disclosure may be similarly applied to a case where another computer or server executes the program, or a case where these cooperate with each other to execute the program.

Figure 20:
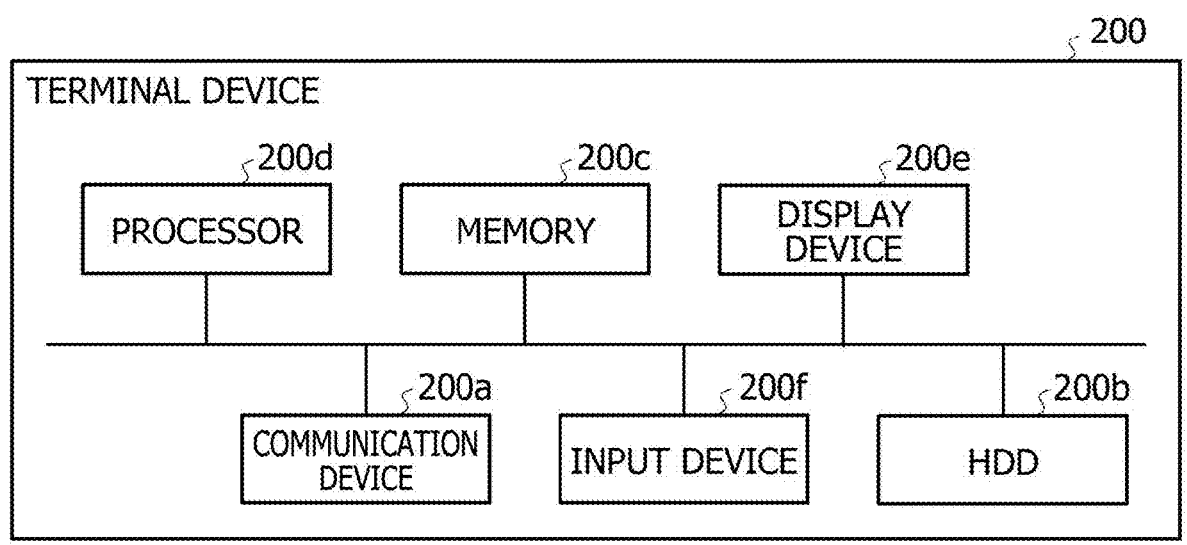
FIG. 20 is a diagram for explaining a hardware configuration example.

This program may be distributed via a network such as the Internet. In addition, this program may be recorded on a computer-readable recording medium such as a hard disk, a flexible disk (FD), a compact disc read-only memory (CD-RO), a magneto-optical disk (MO), a digital versatile disc (DVD), or the like and may be executed by being read by a computer from the recording medium. FIG. 20 is a diagram for explaining a hardware configuration example. As illustrated in FIG. 20, the terminal device 200 includes a communication device 200a, an HDD 200b, a memory 200c, a processor 200d, a display device 200e, and an input device 200f. Further, the respective units illustrated in FIG. 20 are interconnected by a bus or the like.

The communication device 200a is a network interface card or the like, and communicates with other servers. The HDD 200b stores a program and DB for operating the functions illustrated in FIG. 1B.

The processor 200d operates a process that executes each function described with reference to FIG. 1B, etc. by reading a program that executes the same processing as each processing unit illustrated in FIG. 1B from the HDD 200b or the like and deploying the program on the memory 200c. That is, this process executes the same function as each processing unit included in the terminal device 200. Specifically, the processor 200d reads, from the HDD 200b or the like, a program having the same functions as the control unit 202, etc. Then, the processor 200d executes a process that executes the same processing as the control unit 202, etc.

In this way, the terminal device 200 operates as an information processing apparatus that executes a data generation method by reading and executing a program. Further, the terminal device 200 may also implement the same functions as those of the above-described embodiments by reading the program from a recording medium by a medium reading device and executing the read program. A program referred to in the third embodiment is not limited to being executed by the terminal device 200. For example, the present disclosure may be similarly applied to a case where another computer or server executes the program, or a case where these cooperate with each other to execute the program.

This program may be distributed via a network such as the Internet. In addition, this program may be recorded on a computer-readable recording medium such as a hard disk, an FD, a CD-ROM, an MO, a DVD, or the like and may be executed by being read by a computer from the recording medium.

According to an aspect of the embodiments, it is possible to provide a training data generation method capable of improving the accuracy of a learning model.

All examples and conditional language recited herein are intended for pedagogical purposes to aid the reader in understanding the invention and the concepts contributed by the inventor to furthering the art, and are to be construed as being without limitation to such specifically recited examples and conditions, nor does the organization of such examples in the specification relate to an illustrating of the superiority and inferiority of the invention. Although the embodiments of the present invention have been described in detail, it should be understood that the various changes, substitutions, and alterations could be made hereto without departing from the spirit and scope of the invention.

What is claimed is:

1. A non-transitory computer-readable recording medium having stored therein a program that causes a computer to execute a process, the process comprising:
    acquiring a first feature from a machine learning model that estimates a first result of a target after a first period in response to an input of a first chronological state of the target in the first period, the first feature being a feature of the first chronological state;
    acquiring a second feature by inputting a second chronological state to the machine learning model, the second feature being a feature of the second chronological state in a second period including a period after the first result is determined;
    generating, based on the first feature and the second feature, training data that takes the second chronological state as an explanatory variable and takes a second result as an objective variable, the second result being obtained by changing the determined first result;
    extracting the first feature from a first piece of training data among plural pieces of training data each including an explanatory variable that indicates plural states of the target and an objective variable that indicates a result corresponding to the plural states, the first piece of training data corresponding to a period before performing a predetermined action on the target, the first feature indicating the feature of the objective variable of the first piece of training data and a correlation among the plural states of the first piece of training data;
    extracting the second feature from a second piece of training data among the plural pieces of training data, the second piece of training data corresponding to a period after performing the predetermined action on the target, the second feature indicating the feature of the objective variable of the second piece of training data and a correlation among the plural states of the second piece of training data; and
    determining whether to change the objective variable of the second piece of training data based on the first feature and the second feature.

2. The non-transitory computer-readable recording medium according to claim 1, wherein
    a neural network is utilized as the learning model, and
    the process further comprises:
    changing parameters of the neural network such that an error between an output result when the explanatory variable is input to the neural network and correct answer information that is the objective variable becomes smaller.

3. The non-transitory computer-readable recording medium according to claim 1, wherein
    the explanatory variable is an attendance category of an employee,
    the objective variable is a presence or absence of recuperation of the employee, and
    the predetermined action is counseling for the employee.

4. The non-transitory computer-readable recording medium according to claim 1, wherein
    the predetermined action is performed on a target corresponding to training data whose teacher label is a positive example such that the teacher label becomes a negative example.

5. The non-transitory computer-readable recording medium according to claim 1, wherein
    the extracting the first feature includes
    calculating a first similarity between a first core tensor and a third core tensor, the first core tensor being a partial pattern that indicates the correlation among the plural states of the first piece of training data and having a feature of the first piece of training data that determines a prediction result, the third core tensor being a core tensor of a piece of training data for which a prediction result is identified,
    the extracting the second feature includes
    calculating a second similarity between a second core tensor and the third core tensor, the second core tensor being a partial pattern that indicates the correlation among the plural states of the second piece of training data and having a feature of the second piece of training data that determines a prediction result, and
    the determining includes changing a teacher label of the objective variable of the second piece of training data when a difference between the first similarity and the second similarity exceeds a preset threshold.

6. The non-transitory computer-readable recording medium according to claim 1, wherein
    the extracting the first feature includes:
    acquiring plural core tensors that are generated based on plural pieces of training data that are used for training of the learning model and assigned with respective teacher labels;
    generating a first core tensor from the first piece of training data; and
    calculating first similarities between the first core tensor and the respective plural core tensors,
    the extracting the second feature includes:
    acquiring the plural core tensors;
    generating a second core tensor from the second piece of training data; and
    calculating second similarities between the second core tensor and the plural core tensors, and
    the determining includes
    determining a teacher label of the objective variable of the second piece of training data based on the first similarities and the second similarities.

7. A training data generation method, comprising:
    acquiring, by a computer, a first feature from a machine learning model that estimates a first result of a target after a first period in response to an input of a first chronological state of the target in the first period, the first feature being a feature of the first chronological state;
    acquiring a second feature by inputting a second chronological state to the machine learning model, the second feature being a feature of the second chronological state in a second period including a period after the first result is determined;
    generating, based on the first feature and the second feature, training data that takes the second chronological state as an explanatory variable and takes a second result as an objective variable, the second result being obtained by changing the determined first result;
    extracting the first feature from a first niece of training data among plural pieces of training data each including an explanatory variable that indicates plural states of the target and an objective variable that indicates a result corresponding to the plural states, the first niece of training data corresponding to a period before performing a predetermined action on the target, the first feature indicating the feature of the objective variable of the first niece of training data and a correlation among the plural states of the first piece of training data;

extracting the second feature from a second piece of training data among the plural pieces of training data, the second niece of training data corresponding to a period after performing the predetermined action on the target, the second feature indicating the feature of the objective variable of the second piece of training data and a correlation among the plural states of the second niece of training data; and determining whether to change the objective variable of the second piece of training data based on the first feature and the second feature.

8. An information processing apparatus, comprising:
a memory; and
a processor coupled to the memory and the processor configured to:
acquire a first feature from a machine learning model that estimates a first result of a target after a first period in response to an input of a first chronological state of the target in the first period, the first feature being a feature of the first chronological state;
acquire a second feature by inputting a second chronological state to the machine learning model, the second feature being a feature of the second chronological state in a second period including a period after the first result is determined;
generate, based on the first feature and the second feature, training data that takes the second chronological state as an explanatory variable and takes a second result as an objective variable, the second result being obtained by changing the determined first result;
extract the first feature from a first piece of training data among plural pieces of training data each including an explanatory variable that indicates plural states of the target and an objective variable that indicates a result corresponding to the plural states, the first piece of training data corresponding to a period before performing a predetermined action on the target, the first feature indicating the feature of the objective variable of the first piece of training data and a correlation among the plural states of the first piece of training data;
extract the second feature from a second piece of training data among the plural pieces of training data, the second piece of training data corresponding to a period after performing the predetermined action on the target, the second feature indicating the feature of the objective variable of the second piece of training data and a correlation among the plural states of the second piece of training data; and
determine whether to change the objective variable of the second piece of training data based on the first feature and the second feature.

9. The information processing apparatus according to claim 8, wherein
the explanatory variable is an attendance category of an employee,
the objective variable is a presence or absence of recuperation of the employee, and
the predetermined action is counseling for the employee.

10. The information processing apparatus according to claim 8, wherein the predetermined action is performed on a target corresponding to training data whose teacher label is a positive example such that the teacher label becomes a negative example.

11. The information processing apparatus according to claim 8, wherein the processor is configured to
calculate a first similarity between a first core tensor and a third core tensor, the first core tensor being a partial pattern that indicates the correlation among the plural states of the first piece of training data and having a feature of the first piece of training data that determines a prediction result, the third core tensor being a core tensor of a piece of training data for which a prediction result is identified to extract the first feature,
calculate a second similarity between a second core tensor and the third core tensor, the second core tensor being a partial pattern that indicates the correlation among the plural states of the second piece of training data and having a feature of the second piece of training data that determines a prediction result to extract the second feature, and
change a teacher label of the objective variable of the second piece of training data when a difference between the first similarity and the second similarity exceeds a preset threshold.

12. The information processing apparatus according to claim 8, wherein the processor is configured to:
acquire plural core tensors that are generated based on plural pieces of training data that are used for training of the learning model and assigned with respective teacher labels;
generate a first core tensor from the first piece of training data; and
calculate first similarities between the first core tensor and the respective plural core tensors to extract the first feature,
acquire the plural core tensors;
generate a second core tensor from the second piece of training data; and
calculate second similarities between the second core tensor and the plural core tensors to extract the second feature, and
determine a teacher label of the objective variable of the second piece of training data based on the first similarities and the second similarities.

13. The training data generation method according to claim 7, wherein
the explanatory variable is an attendance category of an employee,
the objective variable is a presence or absence of recuperation of the employee, and
the predetermined action is counseling for the employee.

14. The training data generation method according to claim 7, wherein
the predetermined action is performed on a target corresponding to training data whose teacher label is a positive example such that the teacher label becomes a negative example.

15. The training data generation method according to claim 7, wherein
the extracting the first feature includes
calculating a first similarity between a first core tensor and a third core tensor, the first core tensor being a partial pattern that indicates the correlation among the plural states of the first piece of training data and having a feature of the first piece of training data that determines a prediction result, the third core tensor being a core tensor of a piece of training data for which a prediction result is identified, the extracting the second feature includes calculating a second similarity between a second core tensor and the third core tensor, the second core tensor being a partial pattern that indicates the correlation among the plural states of the second piece of training data and having a feature of the second piece of training data that determines a prediction result, and the determining includes changing a teacher label of the objective variable of the second piece of training data when a difference between the first similarity and the second similarity exceeds a preset threshold.

16. The training data generation method according to claim 7, wherein the extracting the first feature includes:

acquiring plural core tensors that are generated based on plural pieces of training data that are used for training of the learning model and assigned with respective teacher labels;

generating a first core tensor from the first piece of training data; and calculating first similarities between the first core tensor and the respective plural core tensors, the extracting the second feature includes:

acquiring the plural core tensors;

generating a second core tensor from the second piece of training data; and calculating second similarities between the second core tensor and the plural core tensors, and the determining includes determining a teacher label of the objective variable of the second piece of training data based on the first similarities and the second similarities.

* * * * *